US012048302B2

(12) United States Patent
Patel et al.

(10) Patent No.: US 12,048,302 B2
(45) Date of Patent: *Jul. 30, 2024

(54) PRESERVED TISSUE PRODUCTS AND RELATED METHODS

(71) Applicant: Cook Biotech Incorporated, West Lafayette, IN (US)

(72) Inventors: Umesh H. Patel, West Lafayette, IN (US); Michael L. Taylor, West Lafayette, IN (US); Claus Soendergaard, West Lafayette, IN (US); Cara McCammon, Delphi, IN (US); Rae Ritchie, Lafayette, IN (US)

(73) Assignee: Cook Biotech Incorporated, West Lafayette, IN (US)

( * ) Notice: Subject to any disclaimer, the term of this patent is extended or adjusted under 35 U.S.C. 154(b) by 921 days.

This patent is subject to a terminal disclaimer.

(21) Appl. No.: 16/807,895

(22) Filed: Mar. 3, 2020

(65) Prior Publication Data

US 2020/0375177 A1    Dec. 3, 2020

Related U.S. Application Data

(63) Continuation of application No. 16/190,766, filed on Nov. 14, 2018, now Pat. No. 10,575,516.

(Continued)

(51) Int. Cl.
*A01N 1/02* (2006.01)
*A61K 35/50* (2015.01)
*A61L 27/36* (2006.01)

(52) U.S. Cl.
CPC ......... *A01N 1/0242* (2013.01); *A01N 1/0221* (2013.01); *A01N 1/0263* (2013.01);

(Continued)

(58) Field of Classification Search
CPC .. A01N 1/0242; A01N 1/0221; A01N 1/0263; A01N 1/0268; A61K 35/50;

(Continued)

(56) References Cited

U.S. PATENT DOCUMENTS

| 5,310,407 A | 5/1994 | Casale |
| 5,795,711 A * | 8/1998 | Mullon ................ A01N 1/0268 435/325 |

(Continued)

FOREIGN PATENT DOCUMENTS

| JP | 2003-009845 A | 1/2003 |
| JP | 2005-194272 | 7/2005 |

(Continued)

OTHER PUBLICATIONS

Abrebaya, A. et al., "Amnion Injections: Evaluating a Brave New World of Regenerative Sports Medicine", Podiatry Management-Sports, Sep. 2016, pp. 67-70.

(Continued)

*Primary Examiner* — Allison M Fox
*Assistant Examiner* — Qing Xu
(74) *Attorney, Agent, or Firm* — Woodard, Emhardt, Henry, Reeves & Wagner, LLP

(57) ABSTRACT

Disclosed are products having animal tissue packed within the lumen of a device such as a needle cannula and being therein impregnated with a cryopreservation medium. The needle cannula or other device can be received in a capsule and/or other container, which in some forms can contain additional amounts of the cryopreservation medium occurring external of the lumen. Methods of use of the products are also described and can include ejecting the animal tissue from the lumen of device using pressurized liquid passed (Continued)

through the lumen, potentially to deliver the animal tissue directly into a patient. Methods of manufacture of the products are also described.

20 Claims, 6 Drawing Sheets

Related U.S. Application Data

(60) Provisional application No. 62/586,147, filed on Nov. 14, 2017.

(52) U.S. Cl.
CPC ............ *A01N 1/0268* (2013.01); *A61K 35/50* (2013.01); *A61L 27/3604* (2013.01); *A61L 27/3683* (2013.01); *A61L 27/3687* (2013.01)

(58) Field of Classification Search
CPC . A61K 35/48; A61L 27/3604; A61L 27/3683; A61L 27/3687
See application file for complete search history.

(56) References Cited

U.S. PATENT DOCUMENTS

| | | | |
|---|---|---|---|
| 7,850,985 | B2 | 12/2010 | Patel et al. |
| 8,192,763 | B2 | 6/2012 | Johnson |
| 8,470,356 | B2 | 6/2013 | Patel et al. |
| 8,652,216 | B2 | 2/2014 | Chen et al. |
| 8,932,805 | B1 | 1/2015 | Brahm |
| 9,271,817 | B2 | 3/2016 | Dempsey et al. |
| 2003/0187515 | A1 | 10/2003 | Hariri et al. |
| 2003/0236573 | A1 | 12/2003 | Evans et al. |
| 2008/0215087 | A1 | 9/2008 | Pavcnik et al. |
| 2010/0047213 | A1* | 2/2010 | Zeitlin .................. A61P 43/00 435/366 |
| 2011/0256202 | A1 | 10/2011 | Tom et al. |
| 2012/0035743 | A1 | 2/2012 | Young et al. |
| 2012/0141595 | A1 | 6/2012 | Tseng et al. |
| 2012/0183548 | A1* | 7/2012 | Wong ..................... A61P 1/00 435/375 |
| 2013/0084314 | A1 | 4/2013 | Horton et al. |
| 2013/0289715 | A1 | 10/2013 | McFetridge |
| 2014/0031772 | A1* | 1/2014 | Hardy .............. A61B 5/150244 604/319 |
| 2014/0288643 | A1 | 9/2014 | Torres et al. |
| 2014/0341871 | A1 | 11/2014 | Morris et al. |
| 2015/0010506 | A1 | 1/2015 | Jansen et al. |
| 2015/0182669 | A1 | 7/2015 | Walsh |
| 2015/0216910 | A1 | 8/2015 | Horton et al. |
| 2016/0120912 | A1 | 5/2016 | Tseng |
| 2017/0002312 | A1 | 1/2017 | Spencer et al. |

FOREIGN PATENT DOCUMENTS

| | | |
|---|---|---|
| JP | 2010-507462 | 3/2010 |
| JP | 2012-519543 | 8/2012 |
| JP | 2015-532093 | 11/2015 |
| JP | 2016-504101 | 2/2016 |
| JP | 2016-522695 | 8/2016 |
| JP | 2017-513809 | 6/2017 |
| JP | 2017-524419 | 8/2017 |
| WO | WO 2009/125196 A1 | 10/2009 |
| WO | WO 2009/132212 A2 | 10/2009 |
| WO | WO 2016/167332 A1 | 10/2016 |
| WO | WO 2017/062937 A1 | 4/2017 |

OTHER PUBLICATIONS

Allen, C. et al., "Augmented Drive versus Cryopreserved Amniotic Membrane as an Ocular Surface Dressing." Plosone, Oct. 2013, vol. 8, Issue 10, pp. 1-15.

Anderson, J. et al., "The Use of Human Amniotic Allograft on Osteochondritis Dissecans of the Talar Dome: A Comparison with and without Allografts in Arthroscopically Treated Ankles". Sugical Science, 2015, 6, pp. 412-417.

Berger, D. et al., "In Vitro Evaluation of Injectable, Placental Tissue-Derived Products for Interventional Orthopedics." Interventional Orthopedics Foundation.

Cooke, M. et al., "Comparision of cryopreserved amniotic membrane and umbilical cord tissue with dehydrated amniotic membrane/ chorion tissue." Journal of Wound Care, vol. 23, No. 10, Oct. 2014, pp. 1-13.

Duan-Arnold, Y. et al., "Retention of Endogenous Viable Cells Enhances the Anti-Inflammatory Activity of Cryopreserved Amnion". Advances in Wound Case, vol. 4, No. 9, pp. 523-533.

Engels, A. et al., "Collagen plug sealing of iatrogenic fetal membrane defects after fetoscopic surgery for congenital diaphragmatic hernia." Ultrasound Obstet Gynecol, 2014, 43, pp. 54-59.

Hanselman et al. , 'Cryopreserved Human Amniotic Membrane Injection for Plantar Fasciitis: A Randomized, Controlled, Double-Blind Pilot Study', Foot & Ankle International 2015, vol. 36(2) 151-158 DOI: 10.1177/1071100714552824.

International Application No. PCT/US2018/061030 International Search Report and Written Opinion, mailed Mar. 14, 2019, 24 pgs.

International Application No. PCT/US2018/061065 International Search Report and Written Opinion, mailed Feb. 21, 2019, pp. 20.

Jirsova, K et al., "Amniotic membrane in opthalmology: properties, preparation, storage and indications for grafting—a review", Cell and Tissue Banking, vol. 18, No. 2 (Mar. 2, 2017), pp. 193-204, XP055533412.

Kura, T. et al., "Use of Cryopreserved Osteogenic Matric Cell Sheets for Bone Reconstruction", Stem Cell Discovery, vol. 6, No. 01 (Jan. 1, 2016), pp. 13-23, XP055562784.

Lee, ET et al., "Platelet rich plasma and amnion-derived fluid as clinical options for regenerative medicine applications." Journal of Translational Science, 2017, vol. 4(1), pp. 1-3.

Moon et al., 'Successful vitrification of human amnion-derived mesenchymal stem cells', Human Reproduction, vol. 23, Issue 8, Aug. 2008, pp. 1760-1770, Pub.: Jun. 9, 2008.

Pre-Filled Syringes with needle and cap, [online], [retrieved on May 10, 2019]. Retrieved from the Internet: https://www.baxterbiopharmasolutions.com.

Syringe Needle Gauage Chart, Sigma-Aldrich, Lab Basics-Chemicals-Technical Library, [online], [retrieved on May 8, 2019]. Retrieved from the Internet: https://www.sigmaaldrich.com.

Syringe pre-filled with needle and cap, [online], [retrieved on May 10, 2019]. Retrieved from the Internet: https://www.medical-and-lab-supplies.com.

Syringes pre-filled with needles, [online], [retrieved on May 10, 2019]. Retrieved from the Internet: https://www.medical-and-lab-supplies.com.

Thomasen, H. et al., "Comparison of cryopreserved and air-dried human amniotic membrane for ophthalmologic applications." Graefes Arch Clin Exp Ophthalmol, 2009, 247:1691-1700.

Vines, J. et al., "Cryopreserved Amniotic Suspension for the Treatment of Knee Osteoarthritis." The Journal of Knee Surgery, pp. 1-8.

Willett, N. et al., "Intra-articular injection of micronized dehydrated human amnion/chorion membrane attenuates osteoarthritis development." Arthritis research & therapy, 2014, 16:R47, pp. 1-10.

Holland, N. T. et al. Molecular epidemiology biomarkers—sample collection and processing considerations. Toxicology and Applied Pharmacology, vol. 206, No. 2 (Aug. 7, 2005), pp. 261-268. Retrieved from the internet on May 31, 2023, DOI < 10.1016/j.taap.2004.10.024.

Li, T. T. et al. Thermoplastic polyurethanes/polyester/polypropylene composites: Effect of thermoplastic polyurethanes honeycomb structure on acoustic-absorbing and cushioning property. Journal of Industrial Textiles, vol. 462, No. 2 (2016), pp. 578-595.

Paolin, A. et al. Cytokine expression and ultrastructural alterations in fresh-frozen, freeze-dried and y-irradiated human amniotic membranes. Cell and Tissue Banking, vol. 7, No. 3 (Apr. 12, 2016), pp. 399-406.

(56) References Cited

OTHER PUBLICATIONS

Singh, R. et al. Dried gamma-irradiated amniotic membrane as dressing in burn wound care. Journal of Tissue Viability, vol. 20, No. 2 (May 2011), pp. 49-54.

* cited by examiner

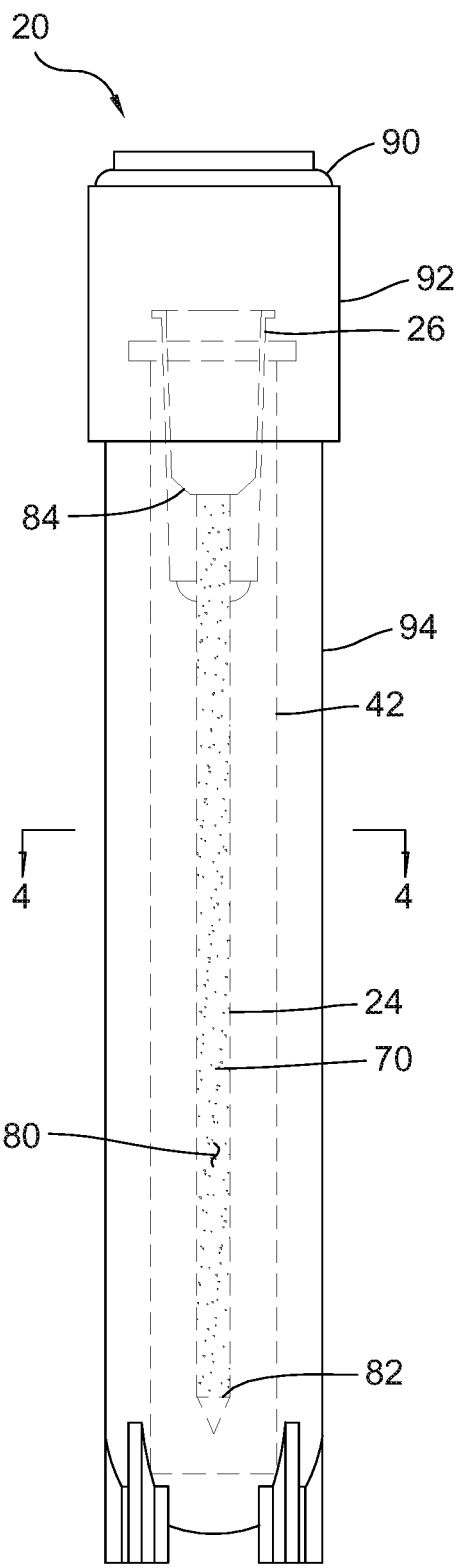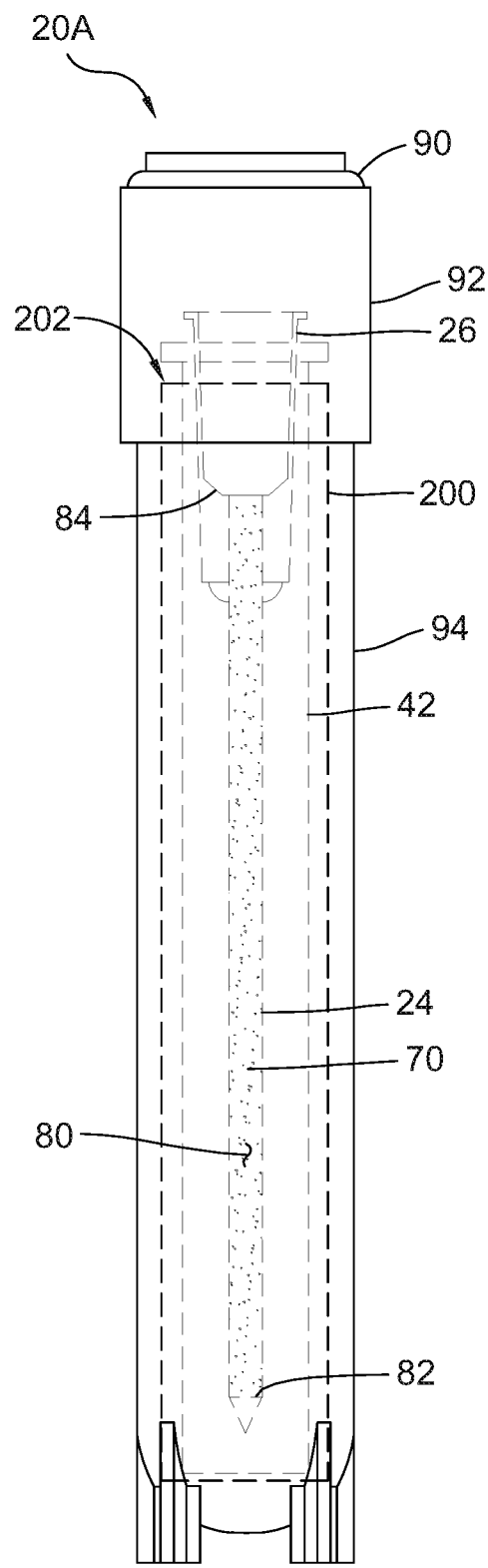
*Fig. 3*  *Fig. 3A*

PRESERVED TISSUE PRODUCTS AND RELATED METHODS

CROSS REFERENCE TO RELATED APPLICATIONS

This application is a continuation of Ser. No. 16/190,766, filed Nov. 14, 2018, which claims the benefit of U.S. Provisional Application No. 62/586,147, filed Nov. 14, 2017, which is hereby incorporated by reference in its entirety.

BACKGROUND

Aspects of the present disclosure relate to preserved tissue products including an animal tissue impregnated with a cryopreservation medium, and to methods for preparing and using such products.

Fresh or preserved animal tissues have long been used in the treatment of patients. For example, placental derived membranes have been used to treat patients in surgical applications. These include both unseparated amnion and chorion, and amnion itself separated from the chorion. The human amnion membrane is the innermost of the fetal membranes deriving from the amniotic sac and constituting the lining of the amniotic cavity. It is approximately 0.02 to 0.5 mm thick. The amnion membrane of the placenta has five layers: a thin layer rests on the basement membrane and contacts the amniotic fluid, an underlying layer of connective tissue attaching the basement membrane that consists of three layers: a compact layer, a layer of fibroblast, and a spongy layer. The spongy layer is adjacent to the cellular layer of the chorion.

Successful preservation of amniotic tissues and other animal tissues has been achieved in a variety of cryopreservation media. These include, as examples, glycerol and Dulbeccos Modified Eagle medium (DMEM) as well as aqueous dimethyl sulfoxide (DMSO) solutions. While preserved tissues have found uses in medicine, those uses have been limited. Needs exist for new preserved animal tissue products that are effective, beneficial and convenient in storage and use.

SUMMARY

In some aspects, the present disclosure relates to animal tissue products having unique configurations and functions in storage and use. In some forms, the products include animal tissue packed within a lumen of a needle or needle assembly, with the lumen containing a cryopreservation medium that impregnates the animal tissue. The products can be readily stored until use is desired, whereupon the products can be conveniently and advantageously processed to recover, and potentially deliver directly into a patient, the animal tissue.

In certain embodiments, the present disclosure provides a preserved tissue product comprising a needle device having a needle device lumen. A sheet of animal tissue is packed within a length of the needle device lumen, and an aqueous cryopreservation medium is provided impregnating the sheet of animal tissue. In preferred form, the preserved tissue product includes:
  a. a needle device, the needle device including:
    i. a needle cannula defining a needle cannula lumen; and
    ii. a needle hub attached to the needle cannula, the needle hub defining a needle hub passageway fluidly connected to the needle cannula lumen;
  b. a sheet of animal tissue (preferably human amniotic tissue) packed within a length of the needle cannula lumen;
  c. an aqueous cryopreservation medium (preferably in a vitrified state) located within the needle cannula lumen and impregnating the sheet of animal tissue;
  d. a capsule having a proximal opening, wherein the proximal opening is fitted over the needle hub to form a needle device/capsule assembly, and wherein the capsule defines a capsule chamber within which the needle cannula is received; and
  e. a storage container defining a storage chamber within which the needle device/capsule assembly is received, the storage container defining a sterile barrier between the storage chamber and environments external of the cryogenic storage container.

In further embodiments, the present disclosure provides a method for providing tissue for implantation, comprising removing the sheet of animal tissue from the needle device lumen or needle cannula lumen of a preserved tissue product as discussed above and/or elsewhere herein. Where the cryopreservation medium that is present is vitrified, the method can also include thawing the preserved tissue product to liquefy the vitrified cryopreservation medium prior to the removing. The removing can include forcing the sheet of tissue out of the needle device lumen or needle cannula lumen with pressurized liquid (e.g. as driven by a syringe or pump). A tip of the needle cannula can be located within a patient when the forcing is conducted, to deliver the sheet of animal tissue directly into the patient.

In still further embodiments, the present disclosure provides a method for making a preserved tissue product that includes forcing a sheet of animal tissue into a needle device lumen of a needle device to pack the sheet of animal tissue within a length of the needle device lumen, and providing an aqueous cryopreservation medium impregnating the sheet of animal tissue. The preserved tissue product can be one as discussed above or elsewhere herein. The providing step can be conducted before, during, and/or after the forcing step. The forcing step is beneficially conducted by pulling the sheet of animal tissue into the needle device lumen, for example using a tether such as a length of suture or wire.

Additional embodiments, as well as features and advantages thereof, will be apparent to those of ordinary skill in the art from the descriptions herein.

BRIEF DESCRIPTION OF THE FIGURES

FIG. 3 provides a side elevational view of the embodiment shown in FIG. 1 illustrating in phantom the internally-received needle, amnion and capsule.

FIG. 3A provides side elevational view of an alternative embodiment including the components of the embodiments of FIGS. 1-3 and also a stabilizing support received in the capsule and retaining the needle assembly/capsule combination.

DETAILED DESCRIPTION

Figure 1:
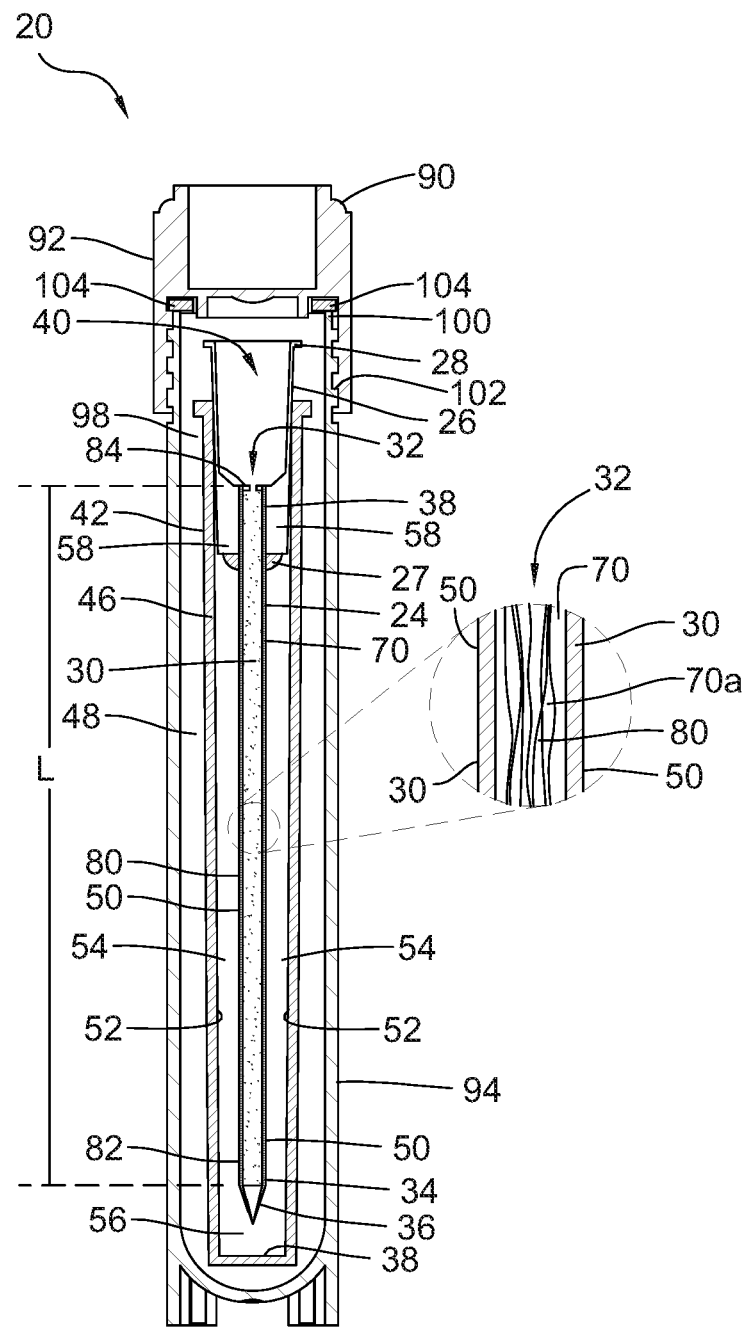
FIG. 1 provides a cross-sectional view of one embodiment of a preserved amniotic tissue product of the present disclosure.
Figure 2:
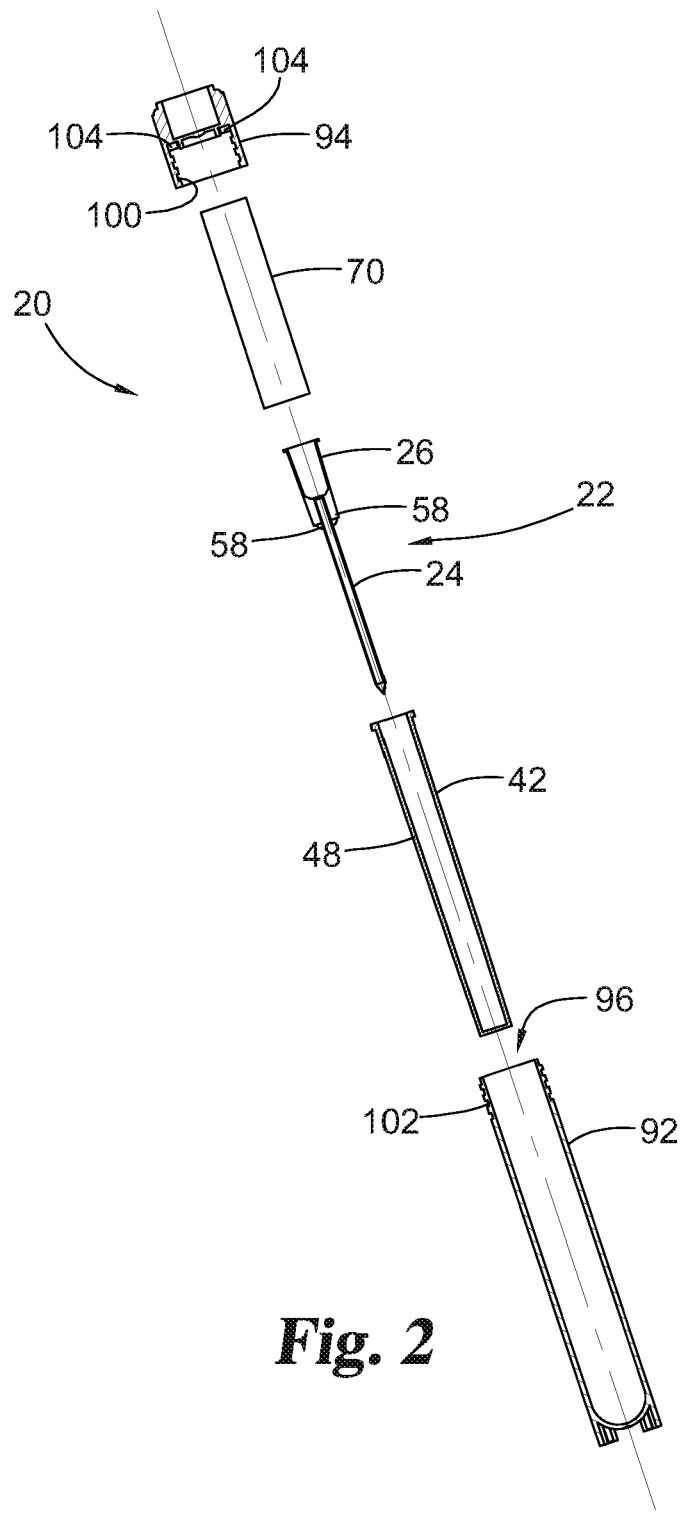
FIG. 2 provides an exploded cross-sectional view of the embodiment shown in FIG. 1.
Figure 4:
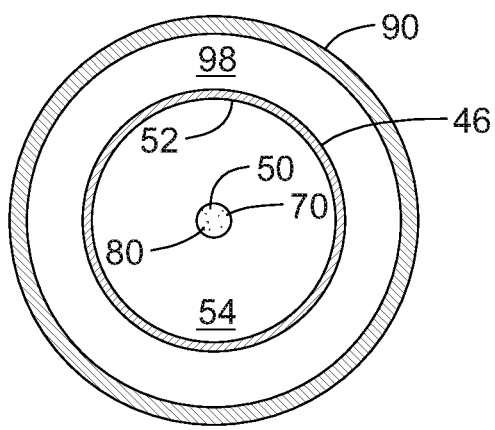
FIG. 4 provides a cross-sectional view taken along line 4-4 of FIG. 3 and viewed in the direction of the arrows.
Figure 5:
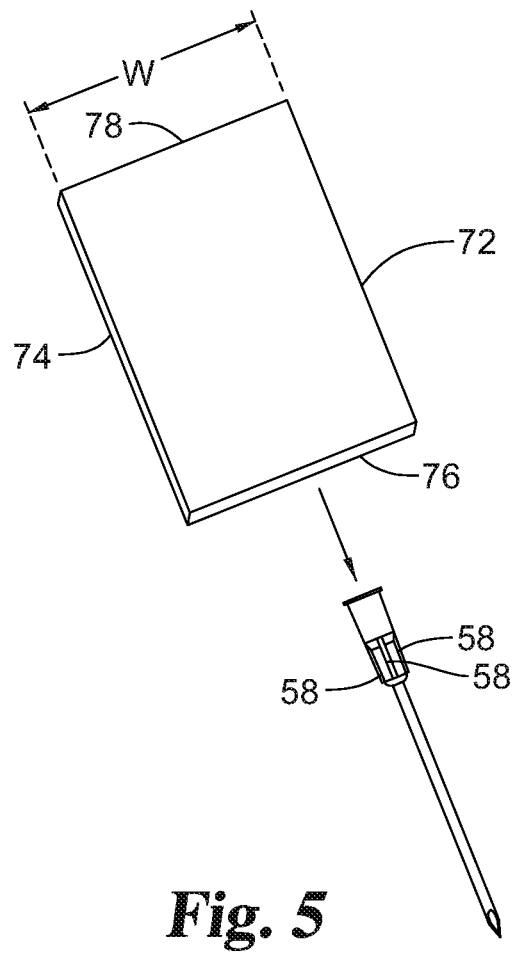
FIG. 5 provides an illustration of a sheet of amniotic tissue and a needle assembly into which it is to be packed.
Figure 6:
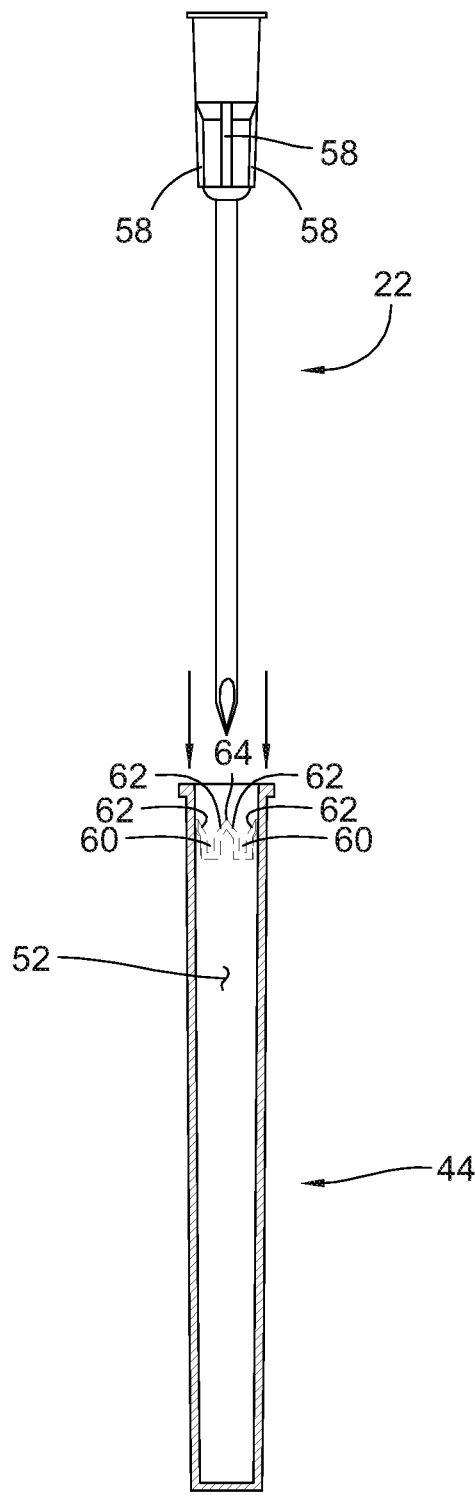
FIG. 6 provides a cross-sectional view of a capsule and a side elevational view of a needle assembly usable in the embodiments of FIGS. 1-5.

While the present invention may be embodied in many different forms, for the purpose of promoting an understanding of the principles of the present invention, reference will now be made to embodiments, some of which are illustrated in the drawings, and specific language will be used to describe the same. It will nevertheless be understood that no limitation of the scope of the invention is thereby intended. Any alterations and further modifications in the described embodiments and any further applications of the principles of the present invention as described herein are contemplated as would normally occur to one skilled in the art to which the invention relates. Additionally, in the detailed description below, numerous alternatives are given for various features related to the structure or composition of materials, or to modes of carrying out methods. It will be understood that each such disclosed alternative, or combinations of such disclosed alternatives, can be combined with the more generalized features discussed in the Summary above, or set forth in the Listing of Certain Embodiments below, to provide additional disclosed embodiments herein.

As disclosed above, aspects of the present disclosure relate to preserved products that include animal tissue packed within a device lumen and a cryopreservation medium within the lumen and impregnating the animal tissue, as well as to methods for preparation and use of such products. In preferred forms, the animal tissue includes a sheet of animal tissue, most preferably human amniotic tissue, and/or the lumen is a lumen of a needle cannula. Additionally, in some forms, the cryopreservation medium can include an externalized portion occurring external of the lumen in which the animal tissue is packed, as well as the cryopreservation medium within the lumen (the "internalized portion"). Also, the needle cannula or other device having the lumen can be received within a capsule, with the externalized portion of the cryopreservation medium occurring between an external surface of the needle cannula or other device and an internal surface of the capsule. Still further, the needle cannula/capsule assembly or combination can be enclosed in an external container, such as a vial, which preferably provides a sterile barrier for the enclosed needle cannula/capsule combination.

With reference now to the drawings, shown in FIGS. 1-6 are views of elements of a first embodiment of a preserved product 20. Product 20 includes generally a needle assembly 22 including a needle cannula 24 and a needle hub 26. An amount of an adhesive or sealant 27 can be provided to facilitate an attachment of the needle cannula 24 to the needle hub 26. Needle hub 26 can have a Luer-lok connecter 28 or other type of connector for fluidly connecting needle assembly 22 to a fluid dispensing device, for example a syringe or pump. The connector can achieve connection through any suitable means or mechanism such as a threaded attachment or friction fit attachment to the fluid dispensing device. Needle cannula 24 includes cannula walls 30, for example circular or otherwise tubular in cross section, defining an internal needle cannula lumen 32. Needle cannula has a distal end 34 defining a tissue penetrating tip 36. Tissue penetrating tip 36 can have any suitable needle tip design, many of which are known. Typically, such needle tip designs include one or more sharp cutting edges defining a leading surface of the tissue penetrating tip 36. Tissue penetrating tip 36 is preferably a non-coring needle tip. Needle cannula 24 includes a proximal end 38 that is connected to needle hub 26 so as to fluidly connect the needle cannula lumen 32 with the interior lumen 40 of the needle hub 26. In this manner, the needle cannula lumen 32 and the interior lumen 40 of the needle hub 26 together define a needle assembly lumen extending through the needle assembly 22 to and out of an opening at the tissue penetrating tip 36. Needle cannula 24 can be composed of any suitable material, and preferably a metal such as stainless steel.

Preserved product 20 also includes a capsule 42 attached to the needle assembly 22 such that the needle cannula 24 is received within the capsule 42. As shown, in one embodiment, this attachment can be provided by an attachment of needle hub 26 to a proximal opening 44 defined by capsule 42. Capsule 42 can include tubular walls 46 of any suitable cross-sectional shape (e.g. circular, ovoid, or polygonal) which define a chamber 48 sized to receive the needle cannula 24. In some forms, attachment of needle hub 26 to proximal opening 44 of capsule 42 suspends the needle cannula 26 within the chamber 48 with exterior surfaces 50 of needle cannula 24 spaced from interior surfaces 52 of walls 46 of capsule 42. In this manner, an intermediate space 54 is defined occurring between exterior lateral surfaces 50 of needle cannula 26 and interior lateral surfaces 52 of walls 46. As well, in some forms, the capsule 42 has a length sufficient to define a distal space 56 occurring between the tissue penetrating tip 36 of needle cannula 22 an a distal interior surface 58 of the capsule 42 when the needle hub 26 is attached to the proximal opening 44 of capsule 42.

The attachment of the needle hub 26 to the proximal opening 44 of capsule 42 can occur by any suitable means or mechanism. In one embodiment, the attachment can be facilitated by a friction fit between a portion of the needle hub 26 and a portion of the capsule 44. In this regard, the needle hub 26 can have an exterior surface that defines a radially projecting flange 58 or multiple radially projecting rectangular flanges 58 (see e.g. FIG. 6) that cooperate with rectangular troughs 60 defined between projecting ridges extending inwardly from the interior surfaces 52 of the walls 46 of capsule 42. For these purposes, forcible insertion of needle hub 26 into proximal opening 44 can encounter increased frictional resistance when the outer surfaces of rectangular flange(s) 58 contact the longitudinally extending projecting ridges defining the rectangular trough(s) 60 (e.g. the rectangular flange(s) 58 can have a width slightly greater than the width of flange(s) 58 such that a friction fit is provided between the two when the flange(s) 58 are received within their corresponding rectangular trough(s) 60). Continued forcible insertion of needle hub 26 into proximal opening 44 to advance flange(s) 58 distally into trough(s) 60 frictionally attaches needle hub 26 to capsule 42. The laterally-extending distal wall (or "bottom wall") of trough (s) 60 can serve as a stop to limit the distance of insertion of the needle assembly 22 into capsule 42, when the these bottom walls contact flange(s) 58 and prevent further distal advancement of the flange(s) 58. Forcible withdrawal of needle hub 26 from proximal opening 44 to overcome frictional resistance between flange(s) 58 and trough(s) 60 causes a release of the attachment of needle hub 26 to the capsule 42. It will be understood that other attachment mechanisms between the capsule 42 and needle hub 26 could also be used, including as illustrative examples other friction fit attachments, detent attachments, and threaded attachments.

In some particular forms, the exterior surface of the hub 26 and the interior surfaces 52 of the capsule 42 can also define a rotational alignment mechanism, by which insertion of the needle hub 26 into the proximal opening 44 can cause rotation of the hub 26 and capsule 42 relative to one another. This relative rotation can longitudinally align flange(s) 58 with trough(s) 60 to facilitate a friction fit, e.g. as discussed above. In the illustrated embodiment, pairs of elongate rails 62 extend inwardly from the interior surfaces 52 of the capsule 42. The pairs of rails 62 define a proximally-projecting peak 64, and the individual rails of each pair of rails 62 diverge from one another as they extend from the peak 64 distally along the capsule 42. The individual rails of the pairs of rails 62 terminate at and join the longitudinally extending ridges defining rectangular troughs 60. As discussed above, troughs 60 participate in the snap fit of needle hub 26 to capsule 42. With the rails 62 and troughs 60 arranged in this manner, an insertion of the needle hub 26 into the proximal opening 44 with flanges 58 not longitudinally aligned with troughs 60 causes the distal ends of flanges 58 to contact and slide along rails of the rail pairs 62, which in turn causes relative rotation between the needle hub 26 (and thereby the needle assembly 22) and the capsule 42. This rotation longitudinally aligns flanges 58 with troughs 60, whereupon continued forcible insertion of the needle hub 26 into opening 44 to advance flanges 58 into troughs 50 effectuates a friction fit.

A (at least one) sheet of human or other animal tissue 70, and preferably of human amniotic tissue, is packed within the needle assembly lumen. In preferred embodiments only a single sheet of human or other animal tissue 70 is packed within the needle assembly lumen. The sheet of animal tissue 70 is preferably packed within the needle cannula lumen 32. In its packed configuration, sheet of animal tissue 70 preferably extends for a length "L" that constitutes at least about 25%, or in other embodiments at least about 50%, or at least about 75%, of the length of the needle cannula lumen 32. Typically, the packed configuration of the sheet of animal tissue 70 extends for a length "L" that constitutes about 25% to about 100% of the length of the needle cannula lumen 32 extending from the distal most edge of tissue penetrating tip 36 to the proximal-most edge of proximal end 38 of needle cannula 24. In addition or alternatively, packed configuration of the sheet of animal tissue 70 can be characterized by one or both of a packing density and a packing ratio as discussed below.

In certain forms, the sheet of animal tissue will have a maximum length L in the range of about 10 mm to about 80 mm and a maximum width W that is less than the length and in the range of about 1.5 mm to about 20 mm, more typically with a maximum length in the range of about 15 mm to about 50 mm and a maximum width that is less than the length and in the range of about 3 mm to about 10 mm. In certain forms, the sheet of animal tissue will be a rectangular sheet having a length L in the range of about 20 to about 50 mm and a width W in the range of about 3 mm to 10 mm. The thickness of the sheet of animal tissue can vary with the particular tissue source and tissue segments selected for recovery and use. In certain embodiments, the average thickness of the sheet of animal tissue will be in the range of about 20 microns to about 200 microns, more typically about 20 microns to about 100 microns. In some forms, a sheet of human amniotic tissue, having the amnion membrane and not the chorion, will have an average thickness in the range of about 30 microns to about 70 microns.

In regard to packing density, the dry weight packing density of the sheet of animal tissue 70 in its packed configuration, calculated as the dry weight of the sheet of animal tissue divided by the volume of the length of the needle cannula lumen occupied by the sheet of animal tissue, can be at least about 0.05 mg tissue/mm$^3$ lumen volume, or at least about 0.1 mg tissue/mm$^3$ lumen volume, and can in some embodiments be in the range of about 0.05 mg tissue/mm$^3$ lumen volume to about 0.9 mg tissue/mm$^3$ lumen volume or in the range of about 0.1 mg tissue/mm$^3$ lumen volume to about 0.7 mg tissue/mm$^3$ lumen volume, or more preferably in the range of about 0.1 mg tissue/mm$^3$ lumen volume to about 0.6 mg tissue/mm$^3$ lumen volume. As an illustrative example, in an embodiment in which a sheet of animal tissue having a dry weight of 3.2 mg is drawn lengthwise into a needle cannula lumen 32 having a circular lumen with a diameter of 0.6 mm (e.g. a 20 gauge needle) to occupy 35 mm of the lumen in its packed configuration, the dry weight packing density would be about 0.32 mg tissue/mm$^3$ lumen volume [3.2 mg of tissue÷$(\pi(0.3)^2 \times 35$ mm$)=3.2$ mg/mm$^3$]. It will be understood that the dry weight packing density referenced herein represents the average packing density for the sheet of animal tissue 70 over the length of the lumen 32 occupied by the tissue, and that the dry weight packing density may differ at points along such length of the lumen 32 (e.g. in an embodiment wherein a wedge-shaped sheet is packed into lumen 32 and has an increasing packing density in the direction toward the wide end of the wedge). In some desirable embodiments, the sheet of animal tissue 70, in its flat configuration, has a substantially constant width (varying by no more than 20%) over at least 50% of its length, over at least 70% of its length, over at least 90% of its length, or over its entire length. In addition or alternatively, the dry weight packing density along at least 50%, at least 70%, at least 90%, or the entirety of the packed length of the sheet of animal tissue 70, can vary by no more than about 10%. It will be understood that while these packing density features are achievable and beneficial in some embodiments, other packing density arrangements are within the contemplation and scope of the disclosed embodiments herein, and for example may be characterized by different widths or thicknesses of the sheet of animal tissue 70 along its length and/or by any doubled-over segments (longitudinally folded segments) of the sheet of animal tissue 70 that occur as a result of the selected packing operation, and/or by any variation of the diameter of lumen 32 along its length in which the sheet of animal tissue 70 is packed.

In regard to packing ratio, the packing ratio of the sheet of animal tissue 70 in its packed configuration, calculated as the surface area of one side of the sheet (e.g. the width multiplied by the length for a rectangular sheet) divided by the volume of the length of the needle cannula lumen 32 occupied by the sheet of animal tissue in its packed configuration, can be at least about 5 mm$^2$ sheet side surface area/mm$^3$ lumen volume, or at least about 10 mm$^2$ sheet side surface area/mm$^3$ lumen volume, and can in some embodiments be in the range of about 5 mm$^2$ sheet side surface area/mm$^3$ to about 40 mm$^2$ sheet side surface area/mm$^3$ lumen volume or in the range of about 10 mm$^2$ sheet side surface area/mm³ lumen volume to about 30 mm² sheet side surface area/mm³ lumen volume, or more preferably in the range of about 15 mm² sheet side surface area/mm³ lumen volume to about 25 mm² sheet side surface area/mm³ lumen volume. As an illustrative example, in an embodiment in which an elongate sheet of animal tissue having a width of 6 mm and a length of 35 mm, is drawn lengthwise into a needle cannula lumen 32 having a circular lumen with a diameter of 0.6 mm (e.g. a 20 gauge needle) to occupy 35 mm of the lumen in its packed configuration, the dry weight packing density would be about 21.2 mm² sheet side surface area/mm³ lumen volume [210 mm² of tissue÷($\pi(0.3)^2 \times 35$ mm)=21.2 mm²/mm³]. It will be understood that while these packing ratio features are achievable and beneficial in some embodiments, other packing ratio arrangements are within the contemplation and scope of the disclosed embodiments herein.

In embodiments in which multiple sheets of animal tissue 70 (e.g. 2, 3 or 4 sheets) are packed within the needle cannula lumen 32, the sheets will be of selected size to pack together within the lumen 32, for example together achieving an overall packing density and/or overall packing ratio as discussed above. It will be understood that reference herein to a packing density, a packing ratio, or another characteristic in relation to "a sheet of animal tissue" or "the sheet of animal tissue", is a reference to an individual sheet of animal tissue (e.g. an individual sheet of amniotic tissue) whether it is the only packed sheet of animal tissue in the lumen 32 or is present with other packed sheets of animal tissue in the lumen 32, whereas reference to an "overall" packing density, an "overall" packing ratio, or an "overall" characteristic in relation to multiple sheets of animal tissue is a reference to all of the sheets considered together.

Various packed configurations of the sheet of animal tissue 70 within the lumen 32 are contemplated. In some forms, the sheet of animal tissue 70 can be in a rolled configuration forming an elongate cylinder, and the cylinder can be packed lengthwise in the lumen 32. In other forms, the sheet of animal tissue 70 can be in a non-rolled configuration such as a gathered, folded and/or twisted configuration.

In some forms, the sheet of animal tissue can have longitudinally-extending folds as packed within the lumen 32. Such longitudinally-extending folds can include preformed folds arranged prior to packing the sheet 70 into lumen (e.g. as in a longitudinally fan-folded sheet 70 pulled or otherwise forced longitudinally into lumen 32), and/or can include random longitudinal folds 70a (see e.g. FIG. 1, enlarged inset) formed as the sheet 70 is gathered upon itself as it is packed longitudinally into lumen 32. In addition to such preformed and/or random longitudinal folds, the packed sheet of animal tissue 70 may have width-wise folds extending across the width dimension of the sheet 70 (extending perpendicular or otherwise transverse to the longitudinal axis of lumen 32). These can occur, for example, when a portion of the length of the sheet 70 is doubled over upon itself in the packed configuration, e.g. such a doubled-over portion may occur at a proximal end of the packed sheet 70, at a distal end of the packed sheet 70, or at both proximal and distal ends of packed sheet 70. These and other forms of the packing configuration for sheet 70 will be apparent to the skilled person from the descriptions herein.

The sheet of animal tissue 70, in its flat (planar) configuration prior to packing within lumen 32, typically has at least one width dimension "W" that is greater than the maximum diameter of lumen 32, more typically at least two times greater than (200% of) the maximum diameter of lumen 32, and even more typically at least three times greater than the maximum diameter of lumen 32. In certain forms, the sheet of animal tissue 70, in its flat (planar) configuration prior to packing within lumen 32, has at least one width dimension W that is about two to about twenty times greater than the maximum diameter of lumen 32, or about three to about fifteen times greater than the maximum diameter of lumen 32, or in some forms about 5 to about 12 times greater than the maximum diameter of lumen 32. As will be understood, such features can provide packed configurations for sheet 70 in which the sheet 70, packed within the lumen 32 of the needle cannula 24, has a packed width that is about 50% or less, or about 33% or less, of its width in its flat condition, and in some embodiments has a packed width of about 5% to about 50%, or about 6.7% to about 33%, or about 8.3% to about 20%, of its width in a flat configuration. In certain preferred embodiments, the diameter of lumen 32 will be substantially constant (e.g. varying by no more than about 10%, or no more than 5%) along the length of the needle cannula 24. Needle cannulas 24 with such substantially constant diameters of lumen 32 can be used with particular benefit in combination with embodiments in which the sheet of animal tissue 70, in its flat (planar) configuration, has a substantially constant width (varying by no more than 20%) over at least 50% of its length, over at least 70% of its length, over at least 90% of its length, or over its entire length, as discussed above.

The lumen 32 of the needle cannula 24 in typical embodiments will have a diameter in the range of about 0.1 mm to about 3 mm (e.g. as can be provided by 32 gauge to 9 gauge needles), or in the range of about 0.3 mm to about 1.6 mm (e.g. as can be provided by 24 gauge to 14 gauge needles), and preferably in the range of about 0.4 mm to about 0.85 mm (e.g. as can be provided by 22 gauge to 18 gauge needles). In certain specific embodiments, the lumen 32 has a diameter of about 0.6 mm (e.g. as can be provided by a 20 gauge needle). In other embodiments, the lumen 32 has a diameter not exceeding about 1.6 mm. In addition or alternatively to the above-specified diameters or diameter ranges, the needle cannula 24 can have a length in the range of about 1 cm to about 8 cm, or in the range of about 2 cm to about 6 cm, and more typically in the range of about 2.5 cm to about 5 cm.

The sheet of animal tissue 70, considered in its flat condition, can have any suitable shape. As examples, the sheet 70 can have a polygonal shape such as a triangular or quadrilateral (e.g. rectangular) shape, a circular shape, an ovoid shape, or an irregular shape. In some forms the sheet 70 is a rectangular shape with two longer sides 72 and 74 and two shorter sides 76 and 78.

An amount of cryopreservation medium 80 is positioned within the lumen 32 and impregnates the sheet of animal tissue 70. In beneficial embodiments, the cryopreservation medium 80 is present in at least the length of needle cannula lumen 32 occupied by the packed sheet of animal tissue 70, extending from the distal packed sheet end 82 to the proximal packed sheet end 84. In some forms the internalized cryopreservation medium 80 can fill the length of needle cannula lumen 32 extending from the tissue penetrating tip 36 to at least the proximal packed sheet end 84, and in some forms beyond packed sheet end 84.

In preferred embodiments, the preserved product 20 also includes an outer container 90, for example a vial, enclosing the needle assembly 24 and capsule 42, preferably within a sterile barrier. Container 90 is preferably a cryogenic container such as a cryogenic vial. In the illustrated embodiment, a vial 90 having a vial cap 92 and a vial body 94 is provided. Vial cap 92 attaches to the opening 96 of vial body 92, for example by friction fit or threaded connection. In preferred forms, attachment of vial cap 94 to vial body 92 forms a chamber 98 in which needle assembly and capsule 42 are contained. As well, in preferred forms the chamber 98 encloses a gaseous environment, for example air, carbon dioxide, or nitrogen. This gaseous environment can provide an insulative barrier around the needle assembly 24 and capsule 42, which can optionally serve to moderate the rate of temperature change of the cryopreservation medium 80 when the product 20 is exposed to a higher or lower temperature than its existing temperature, for example during a freezing and/or a thawing operation as described herein. It will be understood that other arrangements providing an insulative barrier within the vial or other container, including for example foam insulation surrounding at least a portion of the needle assembly 24 and capsule, can also be provided. Illustratively, shown in FIG. 3A is such a product 20A having components corresponding to those for product 20, but also including a foam body 200 (for example a three-dimensionally stable polymeric foam body) received within the vial or other container, the foam body 200 defining an elongate opening 202 sized to frictionally receive outer surfaces of capsule 42. Such frictional receipt of the outer surfaces of capsule 42 can also serve to stabilize the position of the capsule 42/needle assembly 24 combination within the vial or other container, for example holding the capsule 42/needle assembly 24 combination within the chamber 98 in a positioned spaced from the walls of the vial or other container.

In particularly preferred embodiments, the vial 90 forms a sterile barrier isolating chamber 98 from environments external of the vial 90, such that sterile material located within chamber 98 is maintained in a sterile condition, or such that aseptically processed material located within chamber 98 is maintained in its aseptically processed condition. For these purposes in the illustrated embodiment, vial cap 92 can be configured to form a sterile seal with vial body 94 when it is attached to vial body 94, for example by corresponding threads 100 and 102 on the cap 92 and body 94, respectively. In one form, the vial cap 92 can have mounted therein a deformable (e.g. elastomeric) seal member 104, such as a gasket or O-ring, that sterilely seals against surfaces of the vial body 94 when the cap 92 is attached to the body 94, e.g. by threads 100 and 102. Suitable vials for use as vial 90 are available commercially, for example under the tradename Neptune™ cryovials (Neptune Scientific, San Diego, CA, USA).

Figure 7:
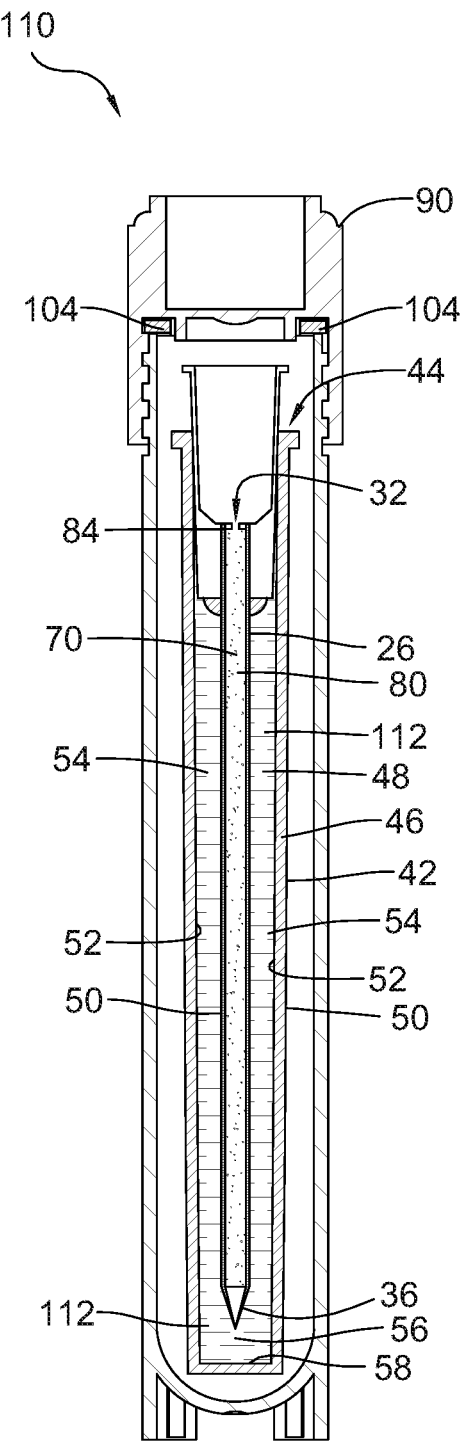
FIG. 7 provides a cross-sectional view of an alternative embodiment including the components of the embodiment of FIGS. 1-3 and cryopreservation medium within the capsule in which the needle assembly is embedded.

Referring now to FIG. 7, shown is another embodiment of a preserved product 110. Preserved product 110 can have components corresponding to those for product 20 (or product 20A), as well as additional features. In the illustrated device of FIG. 7, in addition to the amount of cryopreservation medium 80 located within the lumen 32, an externalized amount of cryopreservation medium 112 is located external of the lumen 32 and within the chamber 48 of capsule 42. Thus, amounts of externalized cryopreservation medium 112 are located in intermediate space 54 between exterior lateral surfaces 50 of needle cannula 24 and interior lateral surfaces 52 of walls 46 of capsule 42. As well, amounts of externalized cryopreservation medium 112 are located in the distal space 56 occurring between the tissue penetrating tip 36 of needle cannula 24 an a distal interior surface 58 of the capsule 42. The externalized cryopreservation medium 112 can thus be in contact with exterior lateral surface 50 of needle cannula, interior lateral surfaces 52 of walls 46, tissue penetrating tip 36 of needle cannula 22, and distal interior surface 58 of capsule 42. The externalized cryopreservation medium 112 and the cryopreservation medium 80 impregnating the sheet of animal tissue can form a continuous phase, communicating through the opening at the tissue penetrating tip 36 of the needle cannula 24.

In some forms, the externalized cryopreservation medium 112 can fill at least a length of intermediate space 54 that is co-extensive with the length of needle cannula lumen 32 occupied by the packed sheet of animal tissue 70, and can fill the chamber 48 of capsule 42 extending from the distal interior surface 58 of capsule 42 to at least a level within the chamber 48 longitudinally aligned with the proximal packed sheet end 84, and in certain embodiments to a level within chamber 48 longitudinally beyond proximal packed sheet end 84.

In some embodiments, the capsule 42 can define a chamber 48 that is closed and liquid-tight except for proximal opening 44. In this manner, upon thawing a preserved product 20 to convert cryopreservation media 80 and 112 from a vitrified state to a flowable liquid state, and maintaining opening 44 in an upward position relative to gravity, the flowable liquid cryopreservation medium can be maintained within capsule 42.

Figure 8:
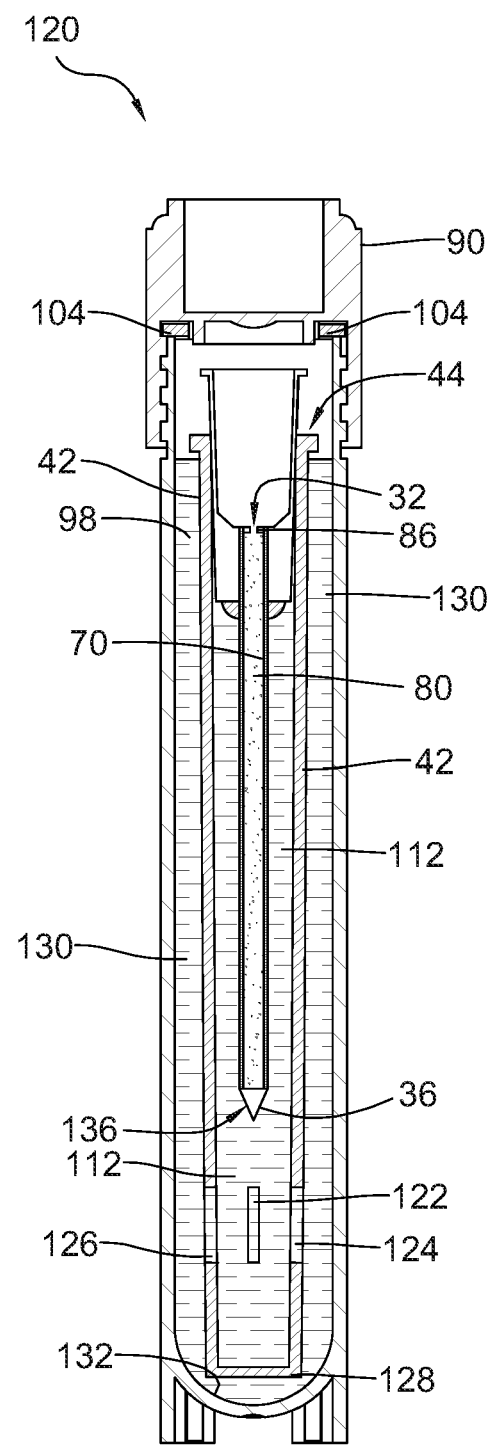
FIG. 8 provides a cross-sectional view of another alternative embodiment in which a capsule has openings and a cryopreservation medium within a vial, a capsule and a needle lumen containing amniotic tissue.

Referring now to FIG. 8, shown is another embodiment of a preserved product 120. Except where otherwise indicated, product 120 can have components corresponding to those of preserved product 20 (or product 20A) discussed above. In product 120, capsule 42 has at least one opening 122, and preferably a plurality of openings 122, 124 and 126, in addition to proximal end opening 44. The opening 122 or openings 122, 124 and 126 preferably occur in the capsule 42 walls at a longitudinal position or longitudinal positions between the longitudinal position of tissue penetrating tip 36 and the distal end 128 of capsule 42. As an alternative to that shown, the capsule 42 can also be like that in preserved product 20 discussed above, except where the capsule has an open distal end. In preserved product 120, the vial or other container 90 contains an amount of cryopreservation medium 130 occurring external of the capsule 42, in addition to amounts 80 and 112 of cryopreservation medium. The cryopreservation medium, including amounts 80, 112 and 130, can be a continuous phase, with these amounts being connected at least through the opening 122 or openings 122, 124 and 126 and the distal end opening 136 of the needle cannula 24. The cryopreservation medium within container 90 preferably fills container 90 from the bottom surface 132 of the chamber 98 to at least a position longitudinally aligned with proximal packed sheet end 86, and in some forms beyond such position. Preserved product 120 thus has an amount of cryopreservation medium 130 additional to that within the capsule 42 (cryopreservation medium amount 112) and needle cannula lumen 32 (cryopreservation medium amount 80), which can provide additional mass during freezing and/or thawing processes, and thereby moderate the rate of temperature change of the sheet of animal tissue 70 and the cryopreservation medium permeating tissue 70, beneficially aiding in the preservation of bioactive factors and/or cell viability within the sheet of animal tissue 70 through these processes.

In some embodiments, the internalized amount of cryopreservation medium 80 and, if present, the externalized amount of cryopreservation medium 112 (embodiment of FIG. 7) and, if present, the externalized amount of cryopreservation medium 130 (embodiment of FIG. 8), is/are in a vitrified state (providing a cryopreserved product), for example at a temperature below 0° C., and preferably below about −20° C. In some forms, the amount of cryopreservation medium 80 (and when present 112 and 130) are at a temperature in the range of about −20° C. to about −200° C., or in the range of about −50° C. to about −196° C., and preferably in the range of about −50° C. to about −100° C. In particular forms, the cryopreservation medium 80 (and when present 112 and 130) are at a temperature in the range of about −50° C. to about −85° C. For these purposes the preserved product 20, 20A, 110 or 120 can be maintained in a cooled environment within appropriate cooling equipment, for example in liquid nitrogen (e.g. at about −196° C.) within a tank or in a mechanical freezer (e.g. at about −75° C. to about −85° C., typically about −80° C.). It will be understood that these and other modes of and equipment for cooling the preserved products to the desired temperature will be available to those skilled in the field based on the teachings herein.

In other embodiments, the internalized amount of cryopreservation medium 80 and, if present, the externalized amount of cryopreservation medium 112, or 112 and 130, is/are in a flowable liquid state. Illustratively, this can occur prior to cooling the cryopreservation medium amount(s) to vitrification temperatures (e.g. as discussed above) and/or after thawing a preserved product to convert vitrified cryopreservation medium amount(s) to flowable liquid amount(s) of cryopreservation medium. As well, in some variants, the preserved products can be stored at cooled temperatures (e.g. about 10° C. or lower, such as about 0° C. to about 10° C.) in which the amount(s) of cryopreservation medium is/are in a liquid state but nonetheless preserve the sheet of animal tissue 70, for example preserve bioactive factors of the sheet of animal tissue 70 and/or viable cells of the sheet of animal tissue 70.

When recovery of the sheet of animal tissue 70 from the product 20, 20A, 110, or 120 is desired, the needle assembly 22 can be disengaged from the capsule 42 and the needle cannula 24 withdrawn from the chamber 48. The sheet of animal tissue 70 can then be recovered from the lumen 32, for example as described herein in discussions above and/or below.

In the manufacture of preserved products herein, the source tissue can be obtained from a suitable human or other animal (e.g. mammalian) donor. While the discussion immediately following refers to the manufacture of human amniotic tissue products from placentas of human donors, it will be understood that for embodiments in which the sheet of animal tissue is other than a placental-derived tissue, the same or similar steps can be used on the appropriate source tissue for the sheet of a selected animal tissue. Also, it will be understood that the steps carried out in the manufacture of the preserved products can be conducted under aseptic or sterile conditions, for example occurring in aseptic or sterile environments, using aseptic or sterile equipment and materials. Such environments can be provided within biocabinets, hoods, or clean rooms, as known to those practiced in the relevant arts.

In certain embodiments, potential human birth tissue donors providing informed consent can be pre-screened including screening of medical records and blood test results. Additionally or alternatively, infectious disease testing of donor blood specimens can be performed for each tissue donor on a specimen collected at the time of donation or within a given period of time (e.g. seven days) prior to or after donation. Candidate infectious disease testing includes, but is not limited to, antibodies to the human immunodeficiency virus, type 1 and type 2 (anti-HIV-1 and anti-HIV-2); nucleic acid test (NAT) for HIV-1; hepatitis B surface antigen (HBsAg); total antibodies to hepatitis B core antigen (anti-HBc—total, meaning IgG and IgM); antibodies to the hepatitis C virus (anti-HCV); NAT for HCV; antibodies to human T-lymphotropic virus type I and type II (anti-HTLV-I and anti-HTLV-II); and syphilis (a non-treponemal or treponemal-specific assay may be performed).

The placenta can be recovered from an aseptic Cesarean delivery or from a vaginal delivery of a newborn. The placental organ, including the placental globe, umbilical cord, associated membranes (chorionic membrane and amniotic membrane), other gelatins, fluids, cells and extracellular matrix can initially be recovered. Optionally, the placental globe, umbilical cord, other gelatins, fluids, cells and extracellular matrix can be immediately removed and discarded. The placenta can also be rinsed, e.g. to remove excess blood and other loose materials.

If it will not be immediately processed further, the placenta can be immersed in a liquid storage medium. The liquid storage medium can be a physiologically acceptable aqueous medium, and contain one or more antimicrobial agents such as gentamycin. Physiologic saline solutions (0.9% NaCl), optionally containing the one or more antibiotics, can be used for the liquid storage medium in some embodiments. In other embodiments, the liquid storage medium can include a cell culture or support medium that contains nutrients, and potentially growth factors, that support viable cells when present, and optionally also one or more antimicrobial agents. The storage medium can be maintained at any suitable temperature, typically at or below about 37° C. In some forms, the liquid storage medium will be cooled, for example at a temperature between 1° C. and 10° C. In other forms, the liquid storage medium will be warmed, for example at a temperature in the range of about 25° C. to 37° C. or about 34° C. to 37° C. As an alternative to storage in a liquid storage medium, the placenta can be stored in a cryopreserved state, for example within a cryopreservation bag in the presence of a suitable cryopreservation medium. The placenta can be stored in the liquid storage medium or in a cryopreserved state for any suitable time, for instance in the liquid storage medium for 1 to 7 days, typically 2-3 days, or in a cryopreserved state for a week to six months. Other times will also be suitable depending on the desired properties of the finished cryopreserved product.

At the point of further processing, in embodiments where the amniotic membrane but not the chorionic membrane is chosen for inclusion in the sheet of amniotic tissue of the cryopreserved product, the chorionic membrane can be separated from the amniotic membrane by blunt dissection. For example, the chorionic membrane may be removed by applying finger pressure and sliding it off of the amniotic membrane using as little pressure as possible to avoid tearing of the amnion. The chorionic membrane and any excess tissue can be discarded in such embodiments. In embodiments where both the amniotic membrane and the chorionic membrane are to be included in the sheet of amniotic tissue, these two membranes can be left attached to one another.

The separated amniotic tissue product (amniotic membrane, chorionic membrane, or both amniotic and chorionic membrane) may be stored immersed in a liquid storage medium until further processed. The liquid storage medium can be a physiologically acceptable aqueous medium, and can in some forms contain one or more antimicrobial agents such as gentamycin. Physiologic saline solutions (0.9% NaCl), optionally containing the one or more antimicrobial agents, can be used for the liquid storage medium in some embodiments. In other embodiments, the liquid storage medium can include a cell culture or support medium that contains nutrients, and potentially growth factors, that support viable cells when present. The liquid storage medium can be maintained at any suitable temperature, typically at or below about 37° C., such as about 1° C. to about 37° C. In some forms, the liquid storage medium will be cooled, for example at a temperature between 1° C. and 10° C. In other forms, the liquid storage medium will be warmed, for example at a temperature in the range of about 25° C. to 37° C. or about 34° C. to 37° C. As an alternative to storage in a liquid storage medium, the recovered membrane product can be stored in a cryopreserved state, for example within a cryopreservation bag in the presence of a suitable cryopreservation medium. The recovered membrane product can be stored in the liquid storage medium or in a cryopreserved state for any suitable time, for instance in the liquid storage medium for 1 to 7 days or in a cryopreserved state for a week to six months. Other times will also be suitable depending on the desired properties of the finished cryopreserved product.

Excess blood and fluids may be liberated from the recovered amniotic tissue sheet product by rinsing. For these purposes, the recovered product can be rinsed with a sterile physiologic saline solution. Multiple rinses may be performed.

In some embodiments, the rinsed amniotic tissue product, be it amnion separated from chorion, or amnion remaining attached to chorion, can be stored immersed in a liquid storage medium until further processed. The liquid storage medium can be a physiologically acceptable aqueous medium, and can in some forms contain one or more antimicrobial agents such as gentamycin. Physiologic saline solutions (0.9% NaCl), optionally containing the one or more antimicrobial agents, can be used for the liquid storage medium in some embodiments. In other embodiments, the liquid storage medium can include a cell culture or support medium that contains nutrients, and potentially growth factors, that support viable cells when present, and optionally also one or more antimicrobial agents. The liquid storage medium can be maintained at any suitable temperature, typically at or below about 37° C., such as about 1° C. to about 37° C. In some forms, the liquid storage medium will be cooled, for example at a temperature between 1° C. and 10° C. In other forms, the liquid storage medium will be warmed, for example at a temperature in the range of about 25° C. to 37° C. or about 34° C. to 37° C. As an alternative to storage in a liquid storage medium, the recovered membrane product can be stored in a cryopreserved state, for example within a cryopreservation bag in the presence of a suitable cryopreservation medium. The rinsed membrane product can be stored in the liquid storage medium or in a cryopreserved state for any suitable time, for instance in the liquid storage medium for 1 to 7 days or in a cryopreserved state for a week to six months. Other times will also be suitable depending on the desired properties of the finished cryopreserved product.

The manner and duration over which the placenta is processed to manufacture the sheet of amniotic tissue can vary and can depend on the properties desired of the sheet of amniotic tissue to be incorporated in the cryopreserved product. In embodiments in which it is desired to retain viable native cells in the sheet of amniotic tissue incorporated in the cryopreserved product, steps can be taken to preserve, to the extent possible or desired, the viability of the native cells. For example, any storage, rinse or other processing media utilized can be selected to support the viability of cells. For these purposes, in some forms, the placenta will be processed to result in the cryopreserved product containing the sheet of amniotic tissue within seven days, or in some particular forms within three days. As well, during storage of the placenta, storage of any intermediate recovered tissue products, and/or during storage of the recovered sheet of amniotic tissue, as discussed above, the tissue involved can be stored in a liquid medium containing nutrients and potentially also growth factors supportive of the viable cells, and potentially also in the presence of a controlled gaseous atmosphere (e.g. 5% carbon dioxide in a humidified atmosphere). In preferred forms, a cell culture medium, for example Dulbecco's modified Eagle's medium (DMEM) (GE Healthcare Life Sciences, Piscataway, NJ), potentially containing one or more antibiotics (e.g. gentamicin, vancomycin, and/or Amphotericin B), can be used as a storage medium for these purposes.

In certain modes of manufacture, a larger sheet of the amniotic tissue is recovered from storage, rinsed if needed to remove any storage medium, and then cut to provide the sheet of amniotic tissue to be packed within the lumen of the needle cannula. Any suitable cutting instrument can be used for these purposes, including instruments used to cut the sheets to be packed one at a time, or instruments such as punches that cut multiple sheets to be packed in a single cutting operation.

Before and/or after being cut from the larger sheet of amniotic tissue, and preferably after rinsing to remove any storage and/or incubation medium, the sheet of amniotic tissue to be packed in the lumen of the needle cannula can be impregnated with a cryopreservation medium, e.g. any of those described herein. For these purposes the sheet of amniotic tissue can be immersed in the cryopreservation medium. Additionally or alternatively, after it is packed within the lumen of the needle cannula, the sheet of amniotic tissue can be impregnated with the cryopreservation medium, for example by passing the cryopreservation medium into the lumen to impregnate the sheet of amniotic tissue, and/or by immersing the needle cannula, with the packed sheet of amniotic tissue, into the cryopreservation medium to cause the medium to enter the lumen and impregnate the sheet of amniotic tissue.

The cut sheets of amniotic tissue to be packed, potentially already impregnated with the cryopreservation medium, are forced into the lumen of the needle cannula using any suitable technique to provide the packed sheet of amniotic tissue. In some modes of manufacture, the sheet of amniotic tissue is pulled into the lumen of the needle cannula using an elongate pulling element sized to pass through the lumen of the needle cannula. The pulling element can be attached to the sheet of amniotic tissue and used to pull the sheet into the lumen of the needle cannula. For these purposes, a suitable tether, such as a length of wire or length of suture, can be used as the pulling element. The suture or other tether can be tied to the sheet of amniotic tissue, preferably adjacent an end thereof, passed through the lumen of the needle cannula (entering first through the hub or through the tissue penetrating tip) to exit the opposite end of the lumen, and then used to pull the sheet of amniotic tissue into the lumen. In preferred forms, as the sheet of amniotic tissue is pulled into the lumen of the needle cannula, the sheet gathers upon itself creating longitudinally-extending folds in the sheet as it is packed within the lumen. This is especially the case when the sheet of amniotic tissue has a lateral width that is greater than the diameter of the lumen of the needle cannula, for example any of those widths disclosed herein relative to the diameter of the lumen. In embodiments in which the sheet of amniotic tissue is impregnated with cryopreservation medium before being packed into the lumen of the needle cannula, as the sheet is forced into the lumen (e.g. by pulling), a portion of the cryopreservation medium impregnating the tissue can be expressed from the tissue, e.g. due to compression of pores of the tissue. Nonetheless, the packed sheet of amniotic tissue remains impregnated with an amount of the cryopreservation medium that is effective in the preservation of biological activities (e.g. viable cells and/or bioactive factors) and/or tissue microarchitecture of the sheet of amniotic tissue.

In other modes of manufacture, the sheet of amniotic tissue can be forced into the lumen of the needle cannula before being impregnated with the cryopreservation medium (e.g. in a dried condition or wetted with another liquid, such as sterile saline), and then the cryopreservation medium can be caused to enter the lumen and impregnate the sheet of amniotic tissue. For these purposes, the needle cannula (or needle assembly including a needle hub and the needle cannula) containing in the needle cannula lumen the packed, non-cryopreservation-medium-loaded sheet, can be immersed in an amount of liquid cryopreservation medium to thereby cause the cryopreservation medium to enter the needle cannula lumen, for example through the tissue penetrating distal end of the needle cannula and/or through the proximal end of the needle cannula. A combination of impregnating the sheet of amniotic tissue before packing in the needle cannula lumen, and of impregnating the packed sheet of amniotic tissue, can also be used. In embodiments of cryopreserved products in which a capsule and/or a vial containing the needle cannula or needle assembly is filled with an amount of cryopreservation medium, the cryopreservation medium in the capsule and/or vial can enter the needle cannula lumen and impregnate the sheet of amniotic tissue, e.g. as the needle cannula is immersed in the cryopreservation medium during assembly of the cryopreserved product (e.g. product 110 or 120 discussed above). An equilibration period prior to vitrifying the cryopreservation medium can be used in some modes of manufacture, to provide time during which the sheet of amniotic tissue is impregnated, or more completely impregnated, with the liquid cryopreservation medium.

In some modes of manufacture, a single elongate sheet of amniotic tissue can be positioned through the lumen of each of multiple needles, after which the sheet of amniotic tissue can be cut to leave a separate segment positioned in the lumen of each of the needles. The individual packed needles can then be processed to products, for example using any of the further techniques disclosed herein. For example, two or more, for example from two to about twenty, or from two to about ten, needles can be held spaced from one another in a fixture with the lumens of each of the needles longitudinally aligned with one another. A pulling element, e.g. as described herein, can be positioned through the aligned lumens of the needles in the fixture, and used to pull the elongate sheet so that it is positioned through the lumen of each of the needles. The sheet can be pulled until the trailing end of the sheet is positioned within the lumen of a first of the needles held in the fixture. The sheet can then be cut at a position proximate to the tissue penetrating tip of such first needle in the fixture, to create a new trailing end of the elongate sheet, and the sheet can then be pulled (e.g. from a position beyond the tip of the last of the needles held in the fixture) until the newly-created trailing end is within the lumen of a second of the needles held in the fixture. The sheet can then be cut at a position proximate to the tissue penetrating tip of such second needle in the fixture. The sequential pulling and cutting operations can then be repeated to pack the lumens of each of the needles held in the fixture. These or other multi-needle packing operations, including automated or semi-automated operations, can be used in the manufacture of packed needles herein. Once packed, the needles can be further processed and/or combined with other elements (e.g. caps and/or vials), for example, using techniques described herein.

While some discussions above concerning forcing (e.g. pulling) the sheet of tissue into the needle cannula lumen and impregnating the tissue with cryopreservation medium focus upon amniotic tissue, it will be understood that the same methods can be used to force other sheets of animal tissue (e.g. as described herein) into the needle cannula lumen, in the preparation of preserved products as described herein.

In certain forms, the sheet of animal tissue is a minimally manipulated human amniotic tissue. In this regard, as used herein, a "minimally manipulated human amniotic tissue" means that the tissue sufficiently retains its native physical integrity, tensile strength, and elasticity to serve as a membranous barrier when placed into or onto a human patient.

The assembled cryopreserved product (e.g. 20, 20A, 110 or 120) is desirably cooled to and maintained at a temperature at which the cryopreservation medium present is in a vitrified state, for example being maintained at temperatures as discussed above using equipment (e.g. liquid nitrogen or a mechanical freezer) as discussed above. In some forms, cooling of the assembled cryopreserved product is performed at a controlled rate, for example at a rate not exceeding 10° C. per minute, or not exceeding 5° C. per minute, or at a rate not exceeding 1° C. per minute. Such controlled cooling can help to preserve the biological activity of the sheet of amniotic tissue, and especially the viability of viable cells, if present or desired in the cryopreserved product. In some forms, the cryopreserved product is effective to maintain a biological activity of the sheet of amniotic tissue, for example bioactive factors and/or viable cells), for at least three months, at least six months, or at least one year, when stored in a cryopreserved condition with the cryopreservation medium in a vitrified state, e.g. at temperatures as taught herein.

As disclosed and discussed above, the sheet of animal tissue is preferably a sheet of human amniotic tissue. The sheet of human amniotic tissue can include human amnion without an attached human chorion layer, or can include human amnion with an attached human chorion layer.

The sheet of human amniotic tissue, or sheet of other animal tissue, can retain amounts of native bioactive factors of the tissue (i.e. endogenous bioactive factors of the tissue, not added bioactive factors). The retained amounts of native bioactive factors of the tissue can include factors that facilitate wound healing, and/or anti-inflammatory factors, and/or other bioactive factors. In some forms, the sheet of amniotic tissue, or sheet of other animal tissue, retains an amount of one or more of, or in some embodiments all of, the following native bioactive factors that facilitate wound healing: Fibroblast Growth Factor-2 (FGF-2), Epidermal Growth Factor (EGF), Transforming Growth Factor-beta, Platelet Derived Growth Factor-AA (PDGF-AA) and Platelet Derived Growth Factor-BB (PDGF-BB).

In the case of a sheet of human amniotic tissue, in certain forms it retains an amount of at least one of, or a mixture of two or more of, or a mixture of three or more of, the following native bioactive factors: EGF, granulocyte colony stimulating factor (GCSF), hepatocyte growth factor (HGF), interleukins 4, 6, 8 and 10 (IL-4, IL-6, IL-8, IL-10), PDGF-AA, PDGF-BB), placental growth factor (PlGF), stromal derived factor 1 alpha (SDF-1α), tissue inhibitors of metalloproteinases 1, 2, and 4 (TIMP-1, TIMP-2, TIMP-4), TGF alpha and beta 1 (TGF-α, TGF-β1), Beta IG-H3, prostaglandin E2 (PGE2), and vascular endothelial growth factor (VEGF). In preferred forms, the sheet of human amniotic tissue retains amounts of all of these native bioactive factors. Other native bioactive factors can be present as well, additional to or in the alternative to the above-listed factors. Studies have shown that processed amniotic tissue can contain hundreds of native bioactive factors. In an embodiment prepared according to the present disclosure, a sheet of aseptically processed human amniotic tissue (without attached chorion) incorporated into a preserved product as discussed above in connection with FIGS. 1-3 and 4-6 and stored under cryopreservation, was removed and tested (7 replicates) using the Ray Biotech Label Based (L-Series) Human Antibody Array 1000 (RayBiotech, Norcross, GA, USA), and was confirmed to retain native bioactive factors.

In some forms, the sheet of human amniotic tissue, or other sheet of animal tissue, can retain amounts of viable native cells of the tissue (i.e. endogenous cells of the tissue, not added cells). The retained viable cells of the tissue can include mesenchymal stem cells, fibroblast cells, endothelial cells, stromal cells, and/or epithelial cells.

In the case of a sheet of human amniotic tissue, in certain forms it retains an amount of at least one of, or at least two of, or all three of, mesenchymal stem cells, fibroblast cells, and epithelial cells.

In the case of a sheet of human amniotic tissue, in certain embodiments the following identifiable structural features can be present in the tissue: an amnion membrane, typically having an average thickness of about 20 to about 50 μm; the presence of native glycosaminoglycans and proteoglycans; the presence of an epithelial basement membrane of the amniotic membrane; and/or the presence of viable epithelial cells on an epithelial basement membrane of the amniotic membrane. As discussed above, in some forms, the human amniotic tissue can further include a chorionic membrane attached to the amniotic membrane.

The sheet of amniotic tissue, or other sheet of animal tissue, can have other characteristics as well. The tissue can include a (at least one) membranous layer of collagenous connective tissue. This membranous layer can be comprised of a network of collagen fibers, wherein the network of collagen fibers retains a native network structure of the tissue. Such a native network structure of the tissue can include collagen fibers that are non-randomly oriented, for instance occurring as generally uniaxial or multi-axial oriented fibers. When it retains amounts of native bioactive factors and/or native viable cells, the sheet of tissue can retain amounts of these bioactive factors and/or amounts of these viable cells interspersed between, upon and/or within the network of collagen fibers.

As discussed above, the sheet of animal tissue is a sheet of human amniotic tissue in particularly preferred embodiments. In other embodiments, the sheet of animal tissue is other than a sheet of human amniotic tissue. As examples, the sheet of animal tissue can in other embodiments be a sheet of submucosal tissue, a sheet of renal capsule membrane tissue, a sheet of dermal collagen tissue, a sheet of dura mater tissue, a sheet of pericardial tissue, a sheet of fascia lata tissue, a sheet of serosal tissue, a sheet of subserous fascia tissue, or a sheet of peritoneal tissue. These or other sheet form tissues may be used as sources for the sheet of animal tissue utilized herein. These tissues may be human tissues, or non-human animal tissues such as non-human mammalian tissues.

As disclosed above, cryopreserved products herein can include an amount of a cryopreservation medium. The cryopreservation medium is preferably an aqueous medium including water and one or more cryopreservatives. The cryopreservation medium can comprise one or more cell-permeating cryopreservatives, one or more non-cell-permeating cryopreservatives, or a combination thereof. In these regards, the cryopreservation medium can comprise one or more cell-permeating cryopreservatives selected from DMSO, a glycerol, a glycol, a propylene glycol, an ethylene glycol, or a combination thereof. In addition or alternatively, the cryopreservation medium can comprise one or more non cell-permeating cryopreservatives selected from polyvinylpyrrolidone, a hydroxyethyl starch, a polysaccharide, a monosaccharides, a sugar alcohol, an alginate, a trehalose, a raffinose, a dextran, or a combination thereof.

In preferred forms, the cryopreservation medium comprises DMSO. For example, DMSO can constitute at least a majority (greater than 50% by weight) of a cell-permeating cryopreservative component of the cryopreservation medium, and in some embodiments the entire cell-permeating component of the cryopreservation medium (i.e. where there is no cell-permeating cryopreservative in the medium other than DMSO). In some variants, the cryopreservation medium will include a 0.1% to 15% (volume/volume, or vol/vol) solution of DMSO in an aqueous medium, potentially including other cryopreservatives or components as discussed herein, more typically in the range of about 0.1% to 12% vol/vol. In some forms, the cryopreservation medium will include a 0.1% to less than 3% vol/vol solution of DMSO in an aqueous medium, or a 0.1% to less than 2% vol/vol solution of DMSO in an aqueous medium, or a 0.1% to less than 1% vol/vol solution of DMSO in an aqueous medium. In other forms, the cryopreservation medium will include a higher amount of DMSO, for example a 3% to 15% vol/vol solution of DMSO in an aqueous medium, or a 5% to 12% vol/vol solution of DMSO in an aqueous medium. In particular embodiments, the cryopreservation medium will include a 10% vol/vol solution of DMSO in an aqueous medium.

The cryopreservation medium can include other substances. For example, it can include albumin (e.g. HSA or BSA), salts, sugars, electrolytes, buffers (e.g. HEPES and/or bicarbonate), or combinations thereof.

Suitable cryopreservation media can be prepared by those skilled in the art or are commercially available. Illustratively, suitable commercially available cryopreservation media are available from BioLife Solutions, Inc. (Bothell, Washington, USA) under the tradename CryoStor® Freeze Media, for example including 5% and 10% DMSO formulations.

Cryopreserved products according to embodiments herein can be thawed for use, during which the vitrified cryopreservation medium will convert to a liquid form. This can be accomplished in any suitable manner. In some forms, the cryopreserved product can be removed from the freezer or other cryopreservation storage equipment and allowed to thaw by exposure to room temperature, while in other forms the cryopreserved product can be warmed in a liquid bath (e.g. at a heated temperature, such as 37° C.), which can for example be set to a constant temperature or progressively warmed to thaw the product. In these or other thawing modes, during the thawing, the cryopreserved product can be thawed as a whole, with the needle assembly/capsule combination remaining received within the vial or other exterior container (potentially maintained with a sterile seal), or the needle assembly/capsule combination can be removed from the vial or other exterior container during thawing with the needle assembly/capsule combination still fitted together, or the needle assembly can be separated from the capsule and vial or other container during thawing. Thawing can be performed over any suitable period of time, for example over a period of time from about 30 seconds to 30 minutes.

In certain manners of use, the needle assembly 22 can be attached to a source of liquid during or after thawing. For example, the hub 26 of the needle assembly 22 can be connected to the source of liquid so that that source of liquid fluidly communicates with the lumen 32 of the needle cannula 24. The source of liquid can for example be a syringe or a pump, or another device configured to deliver the liquid under pressure through the lumen 32 of the needle cannula 24. The syringe, pump or other liquid delivery device can then be operated to force the liquid under pressure through the lumen 32 so as to cause the sheet of tissue 70 to travel distally through lumen 32 and to be ejected from the distal end opening at the tissue penetrating tip 36 of the needle cannula 24. The sheet of tissue 70 can be ejected with the tissue penetrating tip 36 inserted within a patient to directly deliver the sheet of tissue 70 into the patient (e.g. for a therapeutic use as described below), or in other forms with the tip 36 external of the patient (for instance directed into a container such as a tray) to recover the sheet of tissue 70 for use, e.g. for manipulation and administration onto or into tissue of a patient. The liquid of the source of liquid can be the same as the cryopreservation medium (e.g. any of those described herein) or can be a different liquid, for example sterile water or sterile physiologic (0.9%) saline (potentially phosphate buffered saline), or another sterile aqueous medium. The liquid of the source of liquid can also, if desired, include additional therapeutic substances, for example bioactive agents and/or viable cells, which can also be delivered to a patient upon use of the liquid to directly deliver the sheet of tissue 70 into the patient.

The cryopreservation medium 80 impregnating the sheet of tissue 70 can in some forms be delivered (e.g. directly into a patient) along with the sheet of tissue 70 and liquid from the source of liquid used to eject the sheet of tissue 70. In other modes of use, some, all, or essentially all (i.e. 98% or greater), of the amount of cryopreservation medium 80 impregnating the sheet of tissue 70 can be rinsed from the tissue 70 prior to ejection of the tissue 70 from the lumen 32 of the needle cannula 24. This may be accomplished by immersing all or a portion of the needle assembly in a liquid rinse medium such as sterile water, a saline solution or another aqueous medium, one or more times, and potentially with agitation of the rinse medium. In addition or alternatively, in some embodiments, one of these or another liquid rinse medium can be passed through the lumen 32 at a pressure below that which necessary to cause ejection of the sheet of tissue 70, after which the same liquid medium or a different liquid medium can be passed through the lumen 32 at a pressure sufficient to eject the sheet of tissue 70 (now rinsed) from the lumen 32 of the needle cannula 24.

Cryopreserved products as described herein can be used for a variety of purposes, including therapeutic and non-therapeutic (e.g. research) purposes. The sheet(s) of amniotic or other animal tissue can be injected using the needle assembly 22 or otherwise administered to serve as a barrier (e.g. an anti-adhesion barrier) between or within tissue structures of a patient, and/or to promote repair of diseased or damaged tissue (e.g. by injection to promote repair of tunneled or undermined wounds or other injuries). As well, the sheet(s) of amniotic tissue can be injected or otherwise administered to a patient to provide amounts of tissue components such as cells, bioactive factors, extracellular matrix components, or combinations thereof, which can for example have an anti-inflammatory effect by promoting a reduction in the amount and/or activity of pro-inflammatory cytokines and/or by promoting an increase in the amount and/or activity of anti-inflammatory cytokines. In some forms, for these or other purposes, the sheet(s) of amniotic tissue or other animal tissue can be administered in or around joints such as a shoulder, elbow, foot, ankle, knee, hand, wrist or spinal joint.

Listing of Certain Embodiments

The following provides a non-limiting enumerated listing of some of the embodiments disclosed herein.

Embodiment 1. A preserved tissue product, comprising:
a needle device having a needle device lumen;
a sheet of animal tissue, and preferably only a single sheet of animal tissue, packed within a length of the needle device lumen; and
an aqueous cryopreservation medium impregnating the sheet of animal tissue.

Embodiment 2. The preserved tissue product of Embodiment 1, wherein:
the needle device includes a needle cannula defining a needle cannula lumen, and a needle hub attached to the needle cannula, the needle hub defining a needle hub passageway fluidly connected to the needle cannula lumen, wherein the needle cannula lumen and needle hub lumen together define the needle device lumen, and wherein the sheet of animal tissue is packed within a length of the needle cannula lumen.

Embodiment 3. The preserved tissue product of Embodiment 1 or 2, wherein the sheet of animal tissue is a sheet of human amniotic tissue.

Embodiment 4. The preserved tissue product of any preceding Embodiment, wherein the sheet of animal tissue is packed within a length of the needle cannula lumen at a packing ratio in the range of about 5 mm$^2$ sheet side surface area/mm$^3$ lumen volume to about 40 mm$^2$ sheet side surface area/mm$^3$ lumen volume, or about 10 mm$^2$ sheet side surface area/mm$^3$ lumen volume to about 30 mm$^2$ sheet side surface area/mm$^3$ lumen volume, or about 15 mm$^2$ sheet side surface area/mm$^3$ lumen volume to about 25 mm$^2$ sheet side surface area/mm$^3$ lumen volume.

Embodiment 5. The preserved tissue product of any preceding Embodiment, wherein the aqueous cryopreservation medium is vitrified.

Embodiment 6. The preserved tissue product of any one of Embodiments 2 to 5, also comprising a capsule having a proximal opening, wherein the proximal opening is fitted over the needle hub to form a needle device/capsule assembly, and wherein the capsule defines a capsule chamber within which the needle cannula is received.

Embodiment 7. The preserved tissue product of Embodiment 6, also comprising a storage container defining an storage chamber within which the needle device/capsule assembly is received, the storage container defining a sterile barrier between the storage chamber and environments external of the cryogenic storage container.

Embodiment 8. The preserved tissue product of Embodiment 7, wherein the storage container contains a thermally insulative layer of gas or polymeric foam positioned between outer surfaces of the capsule and inner surfaces of the storage container bounding the storage chamber.

Embodiment 9. The preserved tissue product of any one of Embodiments 2 to 8, wherein the needle cannula lumen has a maximum lumen diameter in the range of about 0.1 mm to about 3 mm, or about 0.3 mm to 1.6 mm, or about 0.4 mm to 0.85 mm.

Embodiment 10. The preserved tissue product of any preceding Embodiment, wherein the aqueous cryopreservation medium comprises dimethyl sulfoxide.

Embodiment 11. The preserved tissue product of any one of Embodiments 6 to 10, wherein the capsule has a closed end, an open end, and a body extending between the closed end and the open end.

Embodiment 12. The preserved tissue product of Embodiment 11, wherein a portion of the needle hub of the needle assembly is received within and closes the open end of the elongate capsule.

Embodiment 13. The preserved tissue product of any preceding Embodiment, wherein the sheet of animal tissue comprises viable cells.

Embodiment 14. The preserved tissue product of Embodiment 13, wherein the viable cells are native cells of the sheet of animal tissue.

Embodiment 15. The preserved tissue product of any preceding Embodiment, wherein the sheet of animal tissue retains native bioactive factors.

Embodiment 16. The preserved tissue product of any one of Embodiments 6 to 15, wherein the capsule and needle assembly are attached to one another with a friction fit.

Embodiment 17. The preserved tissue product of Embodiment 16, comprising an insulative layer between an outer surface of the needle cannula and an inner surface of the capsule.

Embodiment 18. The preserved tissue product of Embodiment 17, wherein the insulative layer includes a gas.

Embodiment 19. The preserved tissue product of Embodiment 18, wherein the gas is air.

Embodiment 20. The preserved tissue product of any preceding Embodiment, wherein the sheet of animal tissue includes both amnion and chorion layers.

Embodiment 21. The preserved tissue product of any preceding Embodiment, wherein the sheet of animal tissue includes an amnion layer but not a chorion layer.

Embodiment 22. The preserved tissue product of any preceding Embodiment, wherein the sheet of animal tissue has a maximum width that is at least two times greater than a maximum diameter of the needle cannula lumen.

Embodiment 23. The preserved tissue product of any preceding Embodiment, wherein the sheet of animal tissue is in a non-rolled, gathered configuration.

Embodiment 24. The preserved tissue product of any one of Embodiments 1 to 22, wherein the sheet of animal tissue is in a rolled configuration.

Embodiment 25. The preserved tissue product of any preceding Embodiment, wherein the sheet of animal tissue is fully received within the needle cannula lumen.

Embodiment 26. The preserved tissue product of any preceding Embodiment, wherein the sheet of animal tissue occupies at least 50% of a length of the needle cannula lumen.

Embodiment 27. The preserved tissue product of any preceding Embodiment, wherein the needle cannula lumen has a maximum diameter not exceeding 1.6 mm.

Embodiment 28. The preserved tissue product of any preceding Embodiment, wherein the sheet is packed in the needle cannula lumen at a dry weight packing density in the range of about 0.05 mg tissue/mm$^3$ lumen volume to about 0.9 mg tissue/mm$^3$ lumen volume, or in the range of about 0.1 mg tissue/mm$^3$ lumen volume to about 0.7 mg tissue/mm$^3$ lumen volume, or in the range of about 0.1 mg tissue/mm$^3$ lumen volume to about 0.6 mg tissue/mm$^3$ lumen volume.

Embodiment 29. The preserved tissue product of any preceding Embodiment, wherein the sheet of animal tissue is a minimally manipulated tissue.

Embodiment 30. The preserved tissue product of any preceding Embodiment, wherein the cryopreservation medium comprises DMSO.

Embodiment 31. The preserved tissue product of any preceding Embodiment, wherein the cryopreservation medium comprises 0.1% to about 10% DMSO vol/vol.

Embodiment 32. The preserved tissue product of any preceding Embodiment, wherein the needle cannula is a metal needle cannula, preferably a stainless steel needle cannula.

Embodiment 33. The preserved tissue product of any one of Embodiments 6 to 16 and 20 to 32, wherein the capsule chamber contains an amount of a cryopreservation medium, preferably the same as the cryopreservation medium impregnating the sheet of animal tissue.

Embodiment 34. The preserved tissue product of any one of Embodiments 7 or 9 to 33, wherein the storage chamber contains an amount of a cryopreservation medium, preferably the same as the cryopreservation medium impregnating the sheet of animal tissue.

Embodiment 35. The preserved tissue product of Embodiment 1, also comprising a storage container defining an storage chamber within which the needle device is received, the storage container defining a sterile barrier between the storage chamber and environments external of the storage container.

Embodiment 36. A method for providing tissue for implantation, comprising removing the sheet of animal tissue from the needle device lumen or needle cannula lumen of a preserved tissue product of any one of Embodiments 1 to 35.

Embodiment 37. A method of Embodiment 36, wherein the cryopreservation medium is vitrified, the method also comprising thawing the preserved tissue product to liquefy the vitrified cryopreservation medium prior to said removing.

Embodiment 38. The method of Embodiment 36 or 37, wherein said removing comprises forcing the sheet of tissue out of the needle device lumen or needle cannula lumen with pressurized liquid.

Embodiment 39. The method of Embodiment 38, also comprising fluidly connecting the needle device lumen or needle cannula lumen to a syringe, and wherein said forcing comprises actuating a plunger within a barrel of the syringe to drive pressurized liquid from the barrel and through the needle device lumen or needle cannula lumen.

Embodiment 40. The method of Embodiment 39, wherein during said actuating, a tissue penetrating tip of the needle cannula is positioned within tissue of a patient and said sheet of animal tissue is delivered into the patient.

Embodiment 41. The method of any one of Embodiments 38 to 40, wherein the pressurized liquid has the same composition as the cryopreservation medium.

Embodiment 42. The method of any one of Embodiments 38 to 41, wherein the pressurized liquid is an aqueous liquid.

Embodiment 43. The method of any one of Embodiments 38 to 42, wherein the pressurized liquid comprises DMSO.

Embodiment 44. The method of any one of Embodiments 38 to 43, wherein the pressurized liquid comprises a bioactive agent.

Embodiment 45. The method of any one of Embodiments 38 to 44, wherein the pressurized liquid comprises cells.

Embodiment 46. A method for making a preserved tissue product, comprising:

forcing a sheet of animal tissue into a needle device lumen of a needle device to pack the sheet of animal tissue within a length of the needle device lumen; and providing an aqueous cryopreservation medium impregnating the sheet of animal tissue.

Embodiment 47. The method of Embodiment 46, wherein the preserved tissue product is a preserved tissue product according to any one of Embodiments 1 to 33.

Embodiment 48. The method of Embodiment 46 or 47, wherein said providing is conducted prior to said forcing.

Embodiment 49. The method of Embodiment 46 or 47, wherein said providing is conducted after said forcing.

Embodiment 50. The method of any one of Embodiments 46 to 49, wherein said forcing comprises pulling the sheet of animal tissue into the needle device lumen.

Embodiment 51. The method of Embodiment 50, also comprising attaching a tether to the sheet of animal tissue, and wherein said pulling comprises pulling the tether to pull the sheet of animal tissue into the needle device lumen.

Embodiment 52. The method of any one of Embodiments 46 to 51, wherein the sheet of animal tissue is a sheet of human amniotic tissue, the method also comprising preparing the sheet of human amniotic tissue by a process including separating human amniotic tissue from a placenta, rinsing the human amniotic tissue, and storing the human amniotic tissue in a liquid storage medium containing one or more antibiotics at a temperature in the range of about 34° C. to about 37° C.

The use of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All publications and patent applications cited in this specification are herein incorporated by reference as if each individual publication or patent application were specifically and individually indicated to be incorporated by reference. Further, any theory, mechanism of operation, proof, or finding stated herein is meant to further enhance understanding of the present invention, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

What is claimed is:

1. A preserved tissue product, comprising:

a needle device having a needle device lumen, the needle device comprising a needle cannula defining a needle cannula lumen;

a sheet of animal tissue packed within a length of the needle device lumen, wherein the sheet of animal tissue is packed within a length of the needle cannula lumen at a packing ratio in the range of about 5 mm$^2$ sheet side surface area/mm$^3$ lumen volume to about 40 mm$^2$ sheet side surface area/mm$^3$ lumen volume; and an aqueous cryopreservation medium impregnating the sheet of animal tissue.

2. The preserved tissue product of claim 1, wherein:

the needle device includes a needle cannula defining a needle cannula lumen, and a needle hub attached to the needle cannula, the needle hub defining a needle hub passageway fluidly connected to the needle cannula lumen, wherein the needle cannula lumen and needle hub lumen together define the needle device lumen, and wherein the sheet of animal tissue is packed within a length of the needle cannula lumen.

3. The preserved tissue product of claim 1, wherein the sheet of animal tissue is a sheet of human amniotic tissue.

4. The preserved tissue product of claim 1, wherein the sheet of animal tissue is packed within a length of the needle cannula lumen at a packing ratio in the range of about 10 mm$^2$ sheet side surface area/mm$^3$ lumen volume to about 30 mm$^2$ sheet side surface area/mm$^3$ lumen volume.

5. The preserved tissue product of claim 1, wherein the aqueous cryopreservation medium is vitrified.

6. The preserved tissue product of claim 2, also comprising a capsule having an opening, wherein the opening is fitted over the needle hub to form an assembly of the needle device and capsule, and wherein the capsule defines a capsule chamber within which the needle cannula is received.

7. The preserved tissue product of claim 6, also comprising a storage container defining an storage chamber within which the needle device/capsule assembly is received, the storage container defining a sterile barrier between the storage chamber and environments external of the cryogenic storage container.

8. The preserved tissue product of claim 7, wherein the storage container contains a thermally insulative layer of gas or polymeric foam positioned between outer surfaces of the capsule and inner surfaces of the storage container bounding the storage chamber.

9. The preserved tissue product of claim 2, wherein the needle cannula lumen has a maximum lumen diameter in the range of about 0.1 mm to about 3 mm.

10. The preserved tissue product of claim 1, wherein the aqueous cryopreservation medium comprises dimethyl sulfoxide.

11. The preserved tissue product of claim 6, wherein the capsule has a closed end, an open end, and a body extending between the closed end and the open end.

12. The preserved tissue product of claim 11, wherein a portion of the needle hub of the assembly of the needle device and capsule is received within and closes the open end of the capsule.

13. The preserved tissue product of claim 1, wherein the sheet of animal tissue comprises viable cells.

14. The preserved tissue product of claim 13, wherein viable cells are native cells of the sheet of animal tissue.

15. The preserved tissue product of claim 1, wherein the sheet of animal tissue retains native bioactive factors.

16. The preserved tissue product of claim 1, wherein the sheet of animal tissue does not include a chorion layer.

17. The preserved tissue product of claim 1, wherein the sheet of animal tissue has a maximum width that is at least two times greater than a maximum diameter of the needle cannula lumen.

18. A method for making the preserved tissue product of the claim 1, comprising: forcing a sheet of animal tissue into a needle cannula lumen of a needle device to pack the sheet of animal tissue within a length of the needle cannula lumen, wherein the sheet of animal tissue is packed within the length of the needle cannula lumen at a packing ratio in the range of about 5 mm$^2$ sheet side surface area/mm$^3$ lumen volume to about 40 mm$^2$ sheet side surface area/mm$^3$ lumen volume; and providing an aqueous cryopreservation medium impregnating the sheet of animal tissue, wherein the aqueous cryopreservation medium comprises one or more cryopreservatives for cryopreserving the sheet of animal tissue, thereby making the preserved tissue product of the claim 1.

19. The method of claim 18, wherein said forcing comprises pulling the sheet of animal tissue into the needle cannula lumen.

20. The method of claim 19, also comprising attaching a tether to the sheet of animal tissue, and wherein said pulling comprises pulling the tether to pull the sheet of animal tissue into the needle cannula lumen.

\* \* \* \* \*